US009938353B2

(12) United States Patent
Dinarello et al.

(10) Patent No.: US 9,938,353 B2
(45) Date of Patent: Apr. 10, 2018

(54) COMPOSITIONS, METHODS AND USES FOR ALPHA-1 ANTITRYPSIN FUSION MOLECULES

(75) Inventors: Charles Dinarello, Boulder, CO (US); James D Crapo, Englewood, CO (US); Soohyun Kim, Greenwood Village, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 690 days.

(21) Appl. No.: 14/125,135

(22) PCT Filed: Jun. 22, 2012

(86) PCT No.: PCT/US2012/043869
§ 371 (c)(1),
(2), (4) Date: Apr. 11, 2014

(87) PCT Pub. No.: WO2012/178102
PCT Pub. Date: Dec. 27, 2012

(65) Prior Publication Data
US 2014/0341899 A1 Nov. 20, 2014

Related U.S. Application Data
(60) Provisional application No. 61/500,795, filed on Jun. 24, 2011.

(51) Int. Cl.
C07K 16/40 (2006.01)
C07K 14/81 (2006.01)
C12N 15/62 (2006.01)
A61K 38/57 (2006.01)

(52) U.S. Cl.
CPC .......... *C07K 16/40* (2013.01); *C07K 14/8125* (2013.01); *C12N 15/62* (2013.01); *A61K 38/57* (2013.01); *C07K 2319/30* (2013.01)

(58) Field of Classification Search
CPC ........ C12N 15/00; C12N 15/09; C12N 15/62; C12N 5/10
See application file for complete search history.

(56) References Cited

U.S. PATENT DOCUMENTS

| 4,021,472 A | 5/1977 | Fujii et al. |
| 4,215,051 A | 7/1980 | Schroeder et al. |
| 4,224,342 A | 9/1980 | Fujii |
| 4,283,418 A | 8/1981 | Fujii et al. |
| 4,522,811 A | 6/1985 | Eppstein et al. |
| 4,629,567 A | 12/1986 | Bollen et al. |
| 4,711,848 A | 12/1987 | Insley et al. |
| 4,829,052 A | 5/1989 | Glover et al. |
| 4,829,054 A | 5/1989 | Emerson et al. |
| 4,857,538 A | 8/1989 | Kashman et al. |
| 4,963,654 A | 10/1990 | Katunuma |
| 5,008,242 A | 4/1991 | Lezdey et al. |
| 5,093,316 A | 3/1992 | Lezdey et al. |
| 5,116,964 A | 5/1992 | Capon et al. |
| 5,134,119 A | 7/1992 | Lezdey John et al. |
| 5,157,019 A | 10/1992 | Glover |
| 5,175,253 A | 12/1992 | Fallon et al. |
| 5,216,022 A | 6/1993 | Oleksyszyn |
| 5,346,886 A | 9/1994 | Lezdey |
| 5,420,110 A | 5/1995 | Miller |
| 5,455,165 A | 10/1995 | Capon et al. |
| 5,514,582 A | 5/1996 | Capon et al. |
| 5,514,653 A | 5/1996 | Perlmutter |
| 5,604,201 A | 2/1997 | Thomas et al. |
| 5,604,281 A | 2/1997 | Kamei et al. |
| 5,610,285 A | 3/1997 | Lebing et al. |
| 5,612,194 A | 3/1997 | Rubin et al. |
| 5,616,693 A | 4/1997 | Hwang et al. |
| 5,686,564 A * | 11/1997 | Brundish ............. C07D 211/34 435/13 |
| 5,710,026 A | 1/1998 | Sprecher |
| 5,714,140 A | 2/1998 | Strassmann |
| 5,714,147 A | 2/1998 | Capon et al. |
| 5,734,014 A | 3/1998 | Ishima et al. |
| 5,780,440 A | 7/1998 | Lezdey et al. |
| 5,861,380 A | 1/1999 | Gyorkos et al. |
| 5,869,455 A | 2/1999 | Gyorkos et al. |
| 5,874,424 A | 2/1999 | Batchelor |

(Continued)

FOREIGN PATENT DOCUMENTS

EP 0511188 B1 6/1997
JP 2002506040 A 2/2002

(Continued)

OTHER PUBLICATIONS

AETC Clinical Manual for Management of the HIV-Infected Adult, 2006 Edition, pp. 1-5.
Anderson, Inhibition of HIV-1 gp 160-dependent Membrane Fusion by a Furin-directed Alpha 1-Antitrypsin Variant, The Journal of Biological Chemistry, vol. 268, No. 33 (Nov. 25, 1003), pp. 24887-24891.
Baecher, Allan et al. Human regulatory T cells and their role in autoimmune disease, Immunology Reviews, vol. 212, (2006), pp. 203-216.
Bell, J.J. et al. In Trans T Cell Tolerance Diminishes Autoantibody Responses and Exacerbates Experimental Allergic Encephalomyelitis, The Journal of Immunology, vol. 180 (2008), pp. 1508-1516.
Bollen A, Herzog A, Cravador A, Herion P, Chuchana P, Vander Straten A, Loriau R, Jacobs P, van Elsen A., "Cloning and expression in *Escherichia coli* of full-length complementary DNA coding for human alpha 1-antitrypsin" DNA. Dec. 1983, 2(4): 255-264. doi:10.1089/dna.1983.2.255.
Bowie et al. (Science, 1990, 247:1306-1310).

(Continued)

*Primary Examiner* — Prema M Mertz
(74) *Attorney, Agent, or Firm* — Faegre Baker Daniels LLP

(57) ABSTRACT

Embodiments herein report compositions of alpha-1 antitrypsin fusion polypeptides or peptide derivatives thereof. In certain embodiments, compositions and methods relate to generating a construct of use in pharmaceutically acceptable compositions to treat a subject in need of alpha-1 antitrypsin therapy or treatment. In other embodiments, compositions and methods disclosed herein concern linking alpha-1 antitrypsin or derivative thereof to an immune fragment.

6 Claims, 6 Drawing Sheets

(56) References Cited

U.S. PATENT DOCUMENTS

| | | | |
|---|---|---|---|
| 5,905,023 | A | 5/1999 | Sager et al. |
| 5,985,279 | A | 11/1999 | Waldmann et al. |
| 6,022,855 | A | 2/2000 | Thomas et al. |
| 6,124,257 | A | 9/2000 | Lezdey |
| 6,136,834 | A | 10/2000 | Ohmoto |
| 6,174,859 | B1 | 1/2001 | Lezdey et al. |
| 6,287,817 | B1 | 9/2001 | Davis et al. |
| 6,489,308 | B1 | 12/2002 | Shapiro |
| 6,797,493 | B2 | 9/2004 | Sun et al. |
| 6,849,605 | B1 | 2/2005 | Shapiro |
| 6,924,267 | B2 | 8/2005 | Daemen et al. |
| 7,034,033 | B2 | 4/2006 | Boyce et al. |
| 7,850,970 | B2 | 12/2010 | Shapiro |
| 8,633,305 | B2 | 1/2014 | Shapiro |
| 2002/0081607 | A1 | 6/2002 | Ruben et al. |
| 2003/0040097 | A1 | 2/2003 | Ruben et al. |
| 2003/0069395 | A1 | 4/2003 | Sato et al. |
| 2003/0073217 | A1 | 4/2003 | Barr et al. |
| 2003/0120059 | A1 | 6/2003 | Tao et al. |
| 2003/0190311 | A1 | 10/2003 | Dall'Acqua et al. |
| 2004/0019022 | A1 | 1/2004 | Stec et al. |
| 2004/0220239 | A1 | 11/2004 | Shapiro |
| 2004/0220242 | A1 | 11/2004 | Shapiro |
| 2004/0254349 | A1 | 12/2004 | James et al. |
| 2008/0085854 | A1 | 4/2008 | Barr et al. |
| 2008/0199467 | A1 | 8/2008 | Mjalli et al. |
| 2008/0261869 | A1 | 10/2008 | Shapiro |
| 2009/0203580 | A1 | 8/2009 | Dinarello et al. |
| 2009/0298747 | A1 | 12/2009 | Shapiro |
| 2010/0061979 | A1 | 3/2010 | Blanche et al. |
| 2010/0111940 | A1 | 5/2010 | Flier et al. |
| 2011/0020269 | A1* | 1/2011 | Strom ............... A61K 31/436 424/85.2 |
| 2011/0021416 | A1 | 1/2011 | Shapiro |
| 2011/0053787 | A1 | 3/2011 | Brulliard et al. |
| 2011/0077383 | A1 | 3/2011 | Dall'Acqua et al. |

FOREIGN PATENT DOCUMENTS

| | | | |
|---|---|---|---|
| JP | 2007504144 A | | 3/2007 |
| JP | 2007537992 A | | 12/2007 |
| JP | 2010524971 A | | 7/2010 |
| WO | 8600337 A1 | | 1/1986 |
| WO | 9206706 A1 | | 4/1992 |
| WO | 9318794 A | | 9/1993 |
| WO | 9528422 A | | 10/1995 |
| WO | 9534538 A | | 12/1995 |
| WO | 9721690 A | | 6/1997 |
| WO | 9733996 A | | 9/1997 |
| WO | WO9806248 A2 | | 2/1998 |
| WO | 9823645 A1 | | 6/1998 |
| WO | 9824806 B1 | | 5/1999 |
| WO | 0044390 A1 | | 8/2000 |
| WO | 0052034 A | | 8/2000 |
| WO | 0051625 A | | 9/2000 |
| WO | 0052034 A2 | | 9/2000 |
| WO | WO0051623 A2 | | 9/2000 |
| WO | WO0051624 A2 | | 9/2000 |
| WO | WO0103737 A1 | | 1/2001 |
| WO | WO0202318 A1 | | 1/2002 |
| WO | WO02053092 A2 | | 7/2002 |
| WO | WO02060919 A2 | | 8/2002 |
| WO | 02068455 A2 | | 9/2002 |
| WO | 02094864 A2 | | 11/2002 |
| WO | 02949864 A2 | | 11/2002 |
| WO | 03021273 A2 | | 3/2003 |
| WO | WO03059935 A2 | | 7/2003 |
| WO | 03068934 R | | 8/2003 |
| WO | 2005019434 A2 | | 3/2005 |
| WO | 2005046454 A2 | | 5/2005 |
| WO | 2005047337 A1 | | 5/2005 |
| WO | 2005112970 A2 | | 12/2005 |
| WO | WO2007079312 A2 | | 7/2007 |
| WO | 2008033890 A2 | | 3/2008 |
| WO | WO0051260 A1 | | 9/2008 |
| WO | 2009015345 A1 | | 1/2009 |
| WO | 2010123290 A2 | | 10/2010 |
| WO | 2011102860 A1 | | 8/2011 |
| WO | 2012178102 A2 | | 12/2012 |
| WO | 2013003641 A2 | | 1/2013 |
| WO | 2013003649 A2 | | 1/2013 |

OTHER PUBLICATIONS

Chaiet, Pamela Pam Chaiet Reveals the Latest Tech in the Struggle to Cure Diabetes, The Potomac, Issue 10, (Dec. 14, 2010).
Chan, et al., Alpha-1-antitrypsin (AAT) anomalies are associated with lung disease due to rapidly growing mycobacteria and AAT inhibits Mycobacterium abscessus infection of macrophages, Scandinavian Journal of Infectious Diseases, vol. 39 (2007), pp. 690-696.
Dermer, "Another Anniversary for the War on Cancer," Bio/Technology 1994, 12:320.
Jong, VM, et al., Transplantation tolerance: The concept and its applicability; The Pediatric Transplantation, 3, (1999), pp. 181-192.
Eckman et al. In Vitro Transport of Active A1-Antitrypsin to the Apical Surface of Epithelia by Targeting the Polymeric Immunoglobulin Receptor, Am. J. Respir. Cell Mol. Biol., vol. 21; pp. 246-252 (1999).
eMedicineHealth, Anthrax, Apr. 25, 2007, found at http://www.emedicinehealth.com/script/main/art.asp?articlekey=59372&pf=3&page=7.
Freshney "Culture of Animal Cells, A Manual of Basic Technique," A.R. Liss, Inc., NY, 1983, p. 4.
Gaur et al., "Effect of nasal immunization with protective antigen of Bacillus anthracis on protective immune response against anthrax toxin," Vaccine 2002, 20:2836-39.
George et al.; An Analysis of Protein Domain Linkers: Their Classification and Role in Protein Folding; Protein Engineering, vol. 15(11), pp. 871-879, Nov. 2003.
Goodnow, Christopher C. Pathways for self-tolerance and the treatment of autoimmune diseases. The Lancet, vol. 357 (Jun. 30, 2001), pp. 2115-2121.
Greenspan et al., "Defining epitopes: It's not as easy as it seems," Nature Biotechnology 1999, 17(1):936-37.
Handbook of Targeted Delivery of Imaging Agents. CRC Press, USA, Jan. 1, 1995. pp. 54-55.
Hoppner Clinical Impact of Molecular Diagnostics in Endocrinology (Horm Re. 2002, 58 Suppl. 3:7-15).
Ihse, I., et al. 1876 "Oral trypsin-inhibitor-induced improvement of the exocrine and endocrine pancreatic functions in alloxan diabetic rats," Scandinavian Journal of Gastroenterology, vol. 11, pp. 363-368.
Ikeda, T., et al., 1996, "An inhibition of urinary albumin excretion by protease inhibitor in streptozotocin-diabetic rats," Nephron, vol. 74, No. 4, pp. 709-712.
International Search Report and Written Opinion issued in PCT/US04/27711, dated Jul. 19, 2005. 4 pages.
International Search Report and Written Opinion issued in PCT/US06/22436, dated Feb. 20, 2007, 5 pages.
International Search Report and Written Opinion issued in PCT/US06/61577, dated Jul. 12, 2007, 13 pages.
Janciauskiene et al. (Biochem. Biophys. Res. Comm., 2004, 321:592-600).
Jones TD, Hanlon M, Smith BJ, Heise CT, Nayee PD, Sanders DA, Hamilton A, Sweet C, Unitt E, Alexander G, La KM, Gillies SD, Carr FJ, Baker MP. The development of a modified human IFN-alpha2b linked to the Fc portion of human IgG1 as a novel potential therapeutic for the treatment of hepatitis C virus infection. J Interferon Cytokine Res.
Karnaukhova E, Ophir Y, Golding B. Recombinant human alpha-1 proteinase inhibitor: towards therapeutic use. Amino.
Katsura, M., et al., "Effect of long-term oral administration of trypsin inhibitor on pancreatic exocrine dysfunction in non-insulin dependent diabetes mellitus (NIDDM)", Journal of Pancreas, vol. 7, No. 2, pp. 1-8, 1992, with English translation.

(56) References Cited

OTHER PUBLICATIONS

Kinugasa et al. "Neuroglycan C, A Novel Member of the Neuregulin Family" Biochemical and Biophysical Research Communications, vol. 321(4), pp. 1045-1049, Sep. 3, 2004.
Kraus, T.A. et al., Oral tolerance and inflammatory bowel disease, Current Opinion in Gastroenterology, vol. 21 (2005), pp. 692-696.
Kurachi, K., et. al. Cloning and Sequence of cDNA Coding for Alpha 1-Antitrypsin. Proc. Natl. Acad. Sci., 78(11): 6826-6830, Nov. 1981.
Langner KD, Niedrig M, Fultz P, Anderson D, Reiner G, Repke H, Gelderblom H, Seed B, Hilfenhaus J, Zelllmeissl G. Antiviral effects of different CD4-immunoglobulin constructs against HIV-1 and SIV: immunological characterization, pharmacokinetic data and in vivo experiments. Arch Viral. 1993;130(1-2)157-70.
Lee et al. Effect of Recombinant a1—Antitrypsin Fc-Fused (AAT-Fc_ Protein on the Inibition of Inflammatory Cytokine Production and Streptozotocin-Induced Diabetes; Molecular Medicine vol. 19, Jan. 1, 2013 pp. 65-71.
Leppla et al., "Development of an improved vaccine for anthrax," J Clin Invest 2002, 109:141-44.
Lewis, C. Eli et al., "Alpha-Antitrypsin Monotherapy Prolongs islet Allograft Survival in Mice", Proceedings of the National Academy of Sciences, National Academy of Sciences US, vol. 102 No. 34, Aug. 2005, 6 pages.
Libert et al. Alpha1-Antitrypsin Inhibits the Lethal Response to TNF in Mice; The Journal of Immunology, 1996, 157: 5123-5129.
Lieberman, J., Augmentation therapy reduces frequency of lung infections in antitrypsin deficiency: a new hypothesis with supporting data, Chest, 2000, vol. 118, No. 5, pp. 1480-1485.
Lomas et al., "Commercial plasma alpha 1-antitrypsin (Prolastin) contains a conformationally inactive, latent aomponent," Eur Respir J. 1997, 10(3):672-675.
Lomas, David A., et al., Preparation and Characterization of Latent alpha-1 antitrypsin. Journal of Biological Chemistry, vol. 270, No. 10, (Mar. 10m, 1995) pp. 5282-5288.
Market Letter, Sep. 13, 2009, 2 Pages.
Mast AE, Salvesen G, Schnebli HP, Pizzo SV. Evaluation of the rapid plasma elimination of recombinant alpha 1-proteinase inhibitor: synthesis of polyethylene glycol conjugates with improved therapeutic potential. J Lab Clin Med. 1990; 116(1):58-65.
Michaelsen, et. al. Enhancement of Complement Activation and Cytolysis of Human IgG3 by Deletion of Hinge Exons. Scand. J. Immunol., 32(5):517-528, 1990.
Mohler KM, Torrance DS, Smith CA, Goodwin RG, Stremler KE, Fung VP, Madani H, Widmer MB. Soluble tumor necrosis factor (TNF) receptors are effective therapeutic agents in lethal endotoxemia and function simultaneously as both TNF carriers and TNF antagonists. J Immunol. 1993; 151(3):1548-61.
Musson, J. et al., "Differential Processing of CD4 T-cell epitopes from the protective antigen of Bacillus anthracis," J Biol Chem 2003, 278(52): 52425-52431.
Nakamura, N. et al., Effect of trypsin inhibitor on blood sugar, insulin, and glucagon levfels in normal and streptozotocin rats, Journal of the Kyoto Prefecture University of Medicine, vol. 89, No. 6 (1980) pp. 465-470.
Novak EJ, Blosch CM, Perkins JD, Davis CL, Barr D, McVicar JP, Griffin RS, Farrand AL, Wener M, Marsh CL. Recombinant human tumor necrosis factor receptor Fc fusion protein therapy in kidney transplant recipients undergoing OKT3 induction therapy. Transplantation. 1998; 66(12):1732-5.
O'Riordan et al. a1-Antitrypsin Deficiency-Associated Panniculitis, Departments of Medicine, Pathology, and Transplantation Surgery, Northwestern University Medical School, vol. 63, No. 3, (1996) pp. 1052-1055.
Palomino, Juan Carlos, New Anti-Tuberculosis Drugs: Strategies, Sources and New Molecules, Current Medicinal Chemistry, vol. 16 (2009) pp. 1898-1904.
Panasyuk, A.V., et al., Disseminated Pulmonary Tuberculosis, Sugar Diabetes, and Amyloidosis in a Patient with Hereditary alpha 1-antitrypsin deficiency. Probl. Tuberk., No. 1, (1988) pp. 72-74.

Powell LM, Pain RH.Effects of glycosylation on the folding and stability of human, recombinant and cleaved alpha 1-antitrypsin. J Mol Bioi. 1992 ;224(1):241-52.
Pozzilli, P. et al., No effect of oral insulin on residual beta-cell function in recent-onset Type 1 diabetes (the IMDIABVII), Diabetologia, vol. 43, (2000) pp. 1000-1004.
Request for Ex Parte Reexamination filed Sep. 19, 2014 in connection with U.S. Pat. No. 8,633,305, 79 pages.
Rothe, Helga, et al., IL-18 Inhibits Diabetes Development in Nonobese Diabetic Mice by Counterregulation of Th1-Dependent Destructive Insulitis, The Journal of Immunology, 163 (1999), pp. 1230-1236.
Rutishauser, U., et. al. Amino Acid Sequence of the Fc Region of a Human Gamma G Immunoglobulin. Proc. Natl. Acad. Sci., 61(4): 1414-1421, Dec. 1968.
Sandborn et al. Etanercept for Active Crohn's Disease: A Randomized, Double-Blind, Placebo-Controlled Trial.
Schroeder, Rebecca A. et al., Tolerance and the "Holy Grail" of Transplantation, Journal of Surgical Research, vol. 111, (2003) pp. 109-119.
Schwaiblmair M. Vogelmeier C. Alpha 1-antitrypsin. Hope on the horizon for emphysema sufferers? Drugs Aging.
Seo et al. Concerted Regulation of Inhibitory Activity of a1-Antitrypsin by the Native Strain Distributed Throughout the Molecule.
Shapiro et al., "Alpha-1-antitrypsin inhibits human immunodeficiency virus type 1," FASEB J 2001, 15(1):115-122.
Shimoda, Izumi et al., Physiological Characteristics of Spontaneously Developed Diabetes in Male WBGN/Kob Rat and Prevention of Development of Diabetes by Chronic Oral Administration of Synthetic Trypsin Inhibitor (FOY-305), Pancreas, vol. 8, No. 2, (1993) pp. 196-203.
Simpson et al., "Adenoviral augmentation of elafin protects the lung against acute injury mediated by activated neutrophils and bacterial infection," J Immunol , 2001, 167:1778-86.
Skyler, Jay S. et al., Use of Inhaled Insulin in a Basal/Bolus Insulin Regimen in Type 1 Diabetic Subjects, Diabetes Care vol. 28, (2005) pp. 1630-1635.
Song, S. et al. Recombinant Adeno-Associated Virus-Mediated Alpha-1 Antitrypsin Gene Therapy Prevents Type 1 Diabetes in NOD Mice. Gene Therapy (2004) 11:181-186.
Strom, Terry B., Saving islets from allograft rejection, PNAS, vol. 102, No. 36 (2005) pp. 12651-12652.
Subramaniyam, Devipriya et al. C-36 Peptide, a Degradation Product of Alpha1-Antitrypsin, Modulates Human Monocyte Activation Through LPS Signaling Pathways. The International Journal of Biochemistry & Cell Biology 38:563-575, 2006.
Supplementary European Search Report issued in Application No. 04801916.0 dated Aug. 17, 2016, 3 pages.
Tang et al. Interleukin-17 Antagonism Inhibits Acute But Not Chronic Vascular Rejection1; Transplantation, vol. 348-350, Jul. 27, 2001.
Tania Azam et al. "10 Recombinant Alpha-1 Antitrypsan-Fc (AAT-Fc) Inhibits Candida Induced IL 1beta Secretion from Human CD14 Monocytes Comparison to Plasema-Derive AAT and Capase 1 Inhibition" Cytokine vol. 63. 3, Sep. 1, 2013, p. 245.
Travis et al. Isolation and Properties of Recombinant DNA Produced Variants of Human a1-Proteinase Inhibitor: Journal of Biological Chemistry, vol. 260 (7), pp. 4384-4389, Apr. 10, 1985.
UniProt. Accession No. P01857, Jul. 21, 1986, 2 pages.
Vaerman et al. Complexes of albumin and alpha1-antitrypsin with Fc-fragment of IgA monomer are disulfide-bound to penultimate C-terminal cysteine in the Calpha3-domain. Immunology Letters, 1987, 15, pp. 67-72.
Vaerman, et. al. Complexes of Albumin and Alpha1-Antitrypsin with Fc-Fragment of IgA Monomer are Disulfide-bound to Penultimate C-Terminal Cysteine in the CAlpha3-Domain. Immunology Letters, 15:67-72, 1987.
van Steenbergen, Acta Clinica Belgica 48.3: 1993:171-189.
Vanhove, et. al. Selective Blockade of CD28 and not CTLA-4 with a Single-Chain Fv-Alpha1-Antitrypsin Fusion Antibody. Blood, 102(2):564-570, Jul. 15, 2003.

(56) References Cited

OTHER PUBLICATIONS

Vassar et al. "Beta-Secretase Cleavage of Alzheimer's Amyloid Precursor Protein by the Transmembrane Aspartic Protease Bace" Science, vol. 288 (5440), pp. 735-741, Oct. 22, 1999.
Yang et al (J. Am. Soc. Nephrol. 2003, 14:214-225).
Zamora NP, Pia RV, Del Rio PG, Margaleff RJ, Frias FR, Ronsano JB. Intravenous human plasma-derived augmentation therapy in alpha 1-antitrypsin deficiency: from pharmacokinetic analysis to individualizing therapy. Ann Pharmacother. 2008; 42(5):640-6.
Zettelmeissl G, Gregersen JP, Duport JM, Mehdi S, Reiner G, Seed B. Expression and characterization of human CD4: immunoglobulin fusion proteins. DNA Cell Bioi. 1990; 9(5):347-53.

\* cited by examiner

SEQUENCE LISTING

<160> NUMBER OF SEQ ID NOS: 51

<210> SEQ ID NO 1
<211> LENGTH: 394
<212> TYPE: PRT
<213> ORGANISM: Homo Sapiens

<400> SEQUENCE: 1

| Glu | Asp | Pro | Gln | Gly | Asp | Ala | Ala | Gln | Lys | Thr | Asp | Thr | Ser | His | His |
|---|---|---|---|---|---|---|---|---|---|---|---|---|---|---|---|
| 1 | | | | 5 | | | | | 10 | | | | | 15 | |

| Asp | Gln | Asp | His | Pro | Thr | Phe | Asn | Lys | Ile | Thr | Pro | Asn | Leu | Ala | Glu |
|---|---|---|---|---|---|---|---|---|---|---|---|---|---|---|---|
| | | | 20 | | | | | 25 | | | | | 30 | | |

| Phe | Ala | Phe | Ser | Leu | Tyr | Arg | Gln | Leu | Ala | His | Gln | Ser | Asn | Ser | Thr |
|---|---|---|---|---|---|---|---|---|---|---|---|---|---|---|---|
| | | | 35 | | | | | 40 | | | | | 45 | | |

| Asn | Ile | Phe | Phe | Ser | Pro | Val | Ser | Ile | Ala | Thr | Ala | Phe | Ala | Met | Leu |
|---|---|---|---|---|---|---|---|---|---|---|---|---|---|---|---|
| | 50 | | | | | 55 | | | | | 60 | | | | |

| Ser | Leu | Gly | Thr | Lys | Ala | Asp | Thr | His | Asp | Glu | Ile | Leu | Glu | Gly | Leu |
|---|---|---|---|---|---|---|---|---|---|---|---|---|---|---|---|
| 65 | | | | | 70 | | | | | 75 | | | | | 80 |

| Asn | Phe | Asn | Leu | Thr | Glu | Ile | Pro | Glu | Ala | Gln | Ile | His | Glu | Gly | Phe |
|---|---|---|---|---|---|---|---|---|---|---|---|---|---|---|---|
| | | | | 85 | | | | | 90 | | | | | 95 | |

| Gln | Glu | Leu | Leu | Arg | Thr | Leu | Asn | Gln | Pro | Asp | Ser | Gln | Leu | Gln | Leu |
|---|---|---|---|---|---|---|---|---|---|---|---|---|---|---|---|
| | | | 100 | | | | | 105 | | | | | 110 | | |

| Thr | Thr | Gly | Asn | Gly | Leu | Phe | Leu | Ser | Glu | Gly | Leu | Lys | Leu | Val | Asp |
|---|---|---|---|---|---|---|---|---|---|---|---|---|---|---|---|
| | | | 115 | | | | | 120 | | | | | 125 | | |

| Lys | Phe | Leu | Glu | Asp | Val | Lys | Lys | Leu | Tyr | His | Ser | Glu | Ala | Phe | Thr |
|---|---|---|---|---|---|---|---|---|---|---|---|---|---|---|---|
| | 130 | | | | | 135 | | | | | 140 | | | | |

| Val | Asn | Phe | Gly | Asp | Thr | Glu | Glu | Ala | Lys | Lys | Gln | Ile | Asn | Asp | Tyr |
|---|---|---|---|---|---|---|---|---|---|---|---|---|---|---|---|
| 145 | | | | | 150 | | | | | 155 | | | | | 160 |

| Val | Glu | Lys | Gly | Thr | Gln | Gly | Lys | Ile | Val | Asp | Leu | Val | Lys | Glu | Leu |
|---|---|---|---|---|---|---|---|---|---|---|---|---|---|---|---|
| | | | | 165 | | | | | 170 | | | | | 175 | |

| Asp | Arg | Asp | Thr | Val | Phe | Ala | Leu | Val | Asn | Tyr | Ile | Phe | Phe | Lys | Gly |
|---|---|---|---|---|---|---|---|---|---|---|---|---|---|---|---|
| | | | 180 | | | | | 185 | | | | | 190 | | |

| Lys | Trp | Glu | Arg | Pro | Phe | Glu | Val | Lys | Asp | Thr | Glu | Glu | Glu | Asp | Phe |
|---|---|---|---|---|---|---|---|---|---|---|---|---|---|---|---|
| | | | 195 | | | | | 200 | | | | | 205 | | |

| His | Val | Asp | Gln | Val | Thr | Thr | Val | Lys | Val | Pro | Met | Met | Lys | Arg | Leu |
|---|---|---|---|---|---|---|---|---|---|---|---|---|---|---|---|
| | 210 | | | | | 215 | | | | | 220 | | | | |

| Gly | Met | Phe | Asn | Ile | Gln | His | Cys | Lys | Lys | Leu | Ser | Ser | Trp | Val | Leu |
|---|---|---|---|---|---|---|---|---|---|---|---|---|---|---|---|
| 225 | | | | | 230 | | | | | 235 | | | | | 240 |

| Leu | Met | Lys | Tyr | Leu | Gly | Asn | Ala | Thr | Ala | Ile | Phe | Phe | Leu | Pro | Asp |
|---|---|---|---|---|---|---|---|---|---|---|---|---|---|---|---|
| | | | | 245 | | | | | 250 | | | | | 255 | |

| Glu | Gly | Lys | Leu | Gln | His | Leu | Glu | Asn | Glu | Leu | Thr | His | Asp | Ile | Ile |
|---|---|---|---|---|---|---|---|---|---|---|---|---|---|---|---|
| | | | 260 | | | | | 265 | | | | | 270 | | |

| Thr | Lys | Phe | Leu | Glu | Asn | Glu | Asp | Arg | Arg | Ser | Ala | Ser | Leu | His | Leu |
|---|---|---|---|---|---|---|---|---|---|---|---|---|---|---|---|
| | | 275 | | | | | 280 | | | | | 285 | | | |

| Pro | Lys | Leu | Ser | Ile | Thr | Gly | Thr | Tyr | Asp | Leu | Lys | Ser | Val | Leu | Gly |
|---|---|---|---|---|---|---|---|---|---|---|---|---|---|---|---|
| | 290 | | | | | 295 | | | | | 300 | | | | |

| Gln | Leu | Gly | Ile | Thr | Lys | Val | Phe | Ser | Asn | Gly | Ala | Asp | Leu | Ser | Gly |
|---|---|---|---|---|---|---|---|---|---|---|---|---|---|---|---|
| 305 | | | | | 310 | | | | | 315 | | | | | 320 |

| Val | Thr | Glu | Glu | Ala | Pro | Leu | Lys | Leu | Ser | Lys | Ala | Val | His | Lys | Ala |
|---|---|---|---|---|---|---|---|---|---|---|---|---|---|---|---|
| | | | | 325 | | | | | 330 | | | | | 335 | |

| Val | Leu | Thr | Ile | Asp | Glu | Lys | Gly | Thr | Glu | Ala | Ala | Gly | Ala | Met | Phe |
|---|---|---|---|---|---|---|---|---|---|---|---|---|---|---|---|
| | | | 340 | | | | | 345 | | | | | 350 | | |

| Leu | Glu | Ala | Ile | Pro | Met | Ser | Ile | Pro | Pro | Glu | Val | Lys | Phe | Asn | Lys |
|---|---|---|---|---|---|---|---|---|---|---|---|---|---|---|---|
| | | | | 355 | | | | | 360 | | | | | 365 | |

```
Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Leu Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Phe Val Phe Ala Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Ala Leu Met
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Val Phe Leu Ala
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Val Phe Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide
```

```
<400> SEQUENCE: 7

Phe Leu Met Ile Ile
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Leu
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Val Val
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Leu Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Phe Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Leu Met Phe Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13
```

Phe Met Leu Leu Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Ile Ile Met Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Cys Ile
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Leu Phe Ala Val
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Val Tyr Leu Ile
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Phe Ala Phe Leu Met
1               5

<210> SEQ ID NO 19
<211> LENGTH: 5
<212> TYPE: PRT
<213> ORGANISM: Artificial
<220> FEATURE:
<223> OTHER INFORMATION: synthetic peptide

<400> SEQUENCE: 19

```
Ala Val Phe Leu Met
1               5

<210> SEQ ID NO 20
<211> LENGTH: 10
<212> TYPE: PRT
<213> ORGANISM: Artificial
<220> FEATURE:
<223> OTHER INFORMATION: synthetic peptide

<400> SEQUENCE: 20

Gly Ile Thr Lys Val Phe Ser Asn Gly Ala
1               5                   10

<210> SEQ ID NO 21
<211> LENGTH: 10
<212> TYPE: PRT
<213> ORGANISM: Artificial
<220> FEATURE:
<223> OTHER INFORMATION: synthetic peptide

<400> SEQUENCE: 21

Asp Leu Ser Gly Val Thr Glu Glu Ala Pro
1               5                   10

<210> SEQ ID NO 22
<211> LENGTH: 10
<212> TYPE: PRT
<213> ORGANISM: Artificial
<220> FEATURE:
<223> OTHER INFORMATION: synthetic peptide

<400> SEQUENCE: 22

Leu Lys Leu Ser Lys Ala Val His Lys Ala
1               5                   10

<210> SEQ ID NO 23
<211> LENGTH: 10
<212> TYPE: PRT
<213> ORGANISM: Artificial
<220> FEATURE:
<223> OTHER INFORMATION: synthetic peptide

<400> SEQUENCE: 23

Val Leu Thr Ile Asp Glu Lys Gly Thr Glu
1               5                   10

<210> SEQ ID NO 24
<211> LENGTH: 10
<212> TYPE: PRT
<213> ORGANISM: Artificial
<220> FEATURE:
<223> OTHER INFORMATION: synthetic peptide

<400> SEQUENCE: 24

Ala Ala Gly Ala Met Phe Leu Glu Ala Ile
1               5                   10

<210> SEQ ID NO 25
<211> LENGTH: 10
<212> TYPE: PRT
<213> ORGANISM: Artificial
<220> FEATURE:
<223> OTHER INFORMATION: synthetic peptide

<400> SEQUENCE: 25

Pro Met Ser Ile Pro Pro Glu Val Lys Phe
```

-continued

<210> SEQ ID NO 26
<211> LENGTH: 10
<212> TYPE: PRT
<213> ORGANISM: Artificial
<220> FEATURE:
<223> OTHER INFORMATION: synthetic peptide

<400> SEQUENCE: 26

Asn Lys Pro Phe Val Phe Leu Met Ile Glu
1               5                   10

<210> SEQ ID NO 27
<211> LENGTH: 10
<212> TYPE: PRT
<213> ORGANISM: Artificial
<220> FEATURE:
<223> OTHER INFORMATION: synthetic peptide

<400> SEQUENCE: 27

Gln Asn Thr Lys Ser Pro Leu Phe Met Gly
1               5                   10

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Lys Val Val Asn Pro Thr Gln Lys
1               5

<210> SEQ ID NO 29
<211> LENGTH: 22
<212> TYPE: PRT
<213> ORGANISM: Artificial
<220> FEATURE:
<223> OTHER INFORMATION: synthetic peptide

<400> SEQUENCE: 29

Leu Glu Ala Ile Pro Met Ser Ile Pro Pro Glu Val Lys Phe Asn Lys
1               5                   10                  15

Pro Phe Val Phe Leu Met
            20

<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Leu Glu Ala Ile Pro Met Ser Ile Pro Pro Glu Val Lys Phe Asn Lys
1               5                   10                  15

Pro Phe Val Phe
            20

<210> SEQ ID NO 31
<211> LENGTH: 80
<212> TYPE: PRT
<213> ORGANISM: Artificial
<220> FEATURE:

<223> OTHER INFORMATION: synthetic peptide

<400> SEQUENCE: 31

Gly Ala Asp Leu Ser Gly Val Thr Glu Glu Ala Pro Leu Lys Leu Ser
1               5                   10                  15

Lys Ala Val His Lys Ala Val Leu Thr Ile Asp Glu Lys Gly Thr Glu
            20                  25                  30

Ala Ala Gly Ala Met Phe Leu Glu Ala Ile Pro Met Ser Ile Pro Pro
        35                  40                  45

Glu Val Lys Phe Asn Lys Pro Phe Val Phe Leu Met Ile Glu Gln Asn
    50                  55                  60

Thr Lys Ser Pro Leu Phe Met Gly Lys Val Val Asn Pro Thr Gln Lys
65                  70                  75                  80

<210> SEQ ID NO 32
<211> LENGTH: 652
<212> TYPE: PRT
<213> ORGANISM: Artificial
<220> FEATURE:
<223> OTHER INFORMATION: FC-AAT fusion polypeptide with linker and
      leader sequence
<220> FEATURE:
<221> NAME/KEY: linker between immune molecule and AAT
<222> LOCATION: (419)..(420)

<400> SEQUENCE: 32

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys 245                 250                 255
Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Glu Pro Lys Ser Cys Asp Lys Thr His Thr Cys Pro
            420                 425                 430

Pro Cys Pro Ala Pro Glu Leu Leu Gly Gly Pro Ser Val Phe Leu Phe
        435                 440                 445

Pro Pro Lys Pro Lys Asp Thr Leu Met Ile Ser Arg Thr Pro Glu Val
    450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Ala Leu Pro Ala Pro Ile Glu Lys Thr Ile Ser Lys Ala
    530                 535                 540

Lys Gly Gln Pro Arg Glu Pro Gln Val Tyr Thr Leu Pro Pro Ser Arg
545                 550                 555                 560

Asp Glu Leu Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650

<210> SEQ ID NO 33

<211> LENGTH: 394
<212> TYPE: PRT
<213> ORGANISM: Homo Sapiens

<400> SEQUENCE: 33

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
```

```
385                390
```

<210> SEQ ID NO 34
<211> LENGTH: 36
<212> TYPE: PRT
<213> ORGANISM: Artificial
<220> FEATURE:
<223> OTHER INFORMATION: synthetic peptide

<400> SEQUENCE: 34

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro Thr Gln Lys
        35

<210> SEQ ID NO 35
<211> LENGTH: 62
<212> TYPE: DNA
<213> ORGANISM: Homo sapiens

<400> SEQUENCE: 35
tttagaggcc atacccatgt ctatcccccc cgaggtcaag ttcaacaaac ccctttgtct      60
tt                                                                    62

<210> SEQ ID NO 36
<211> LENGTH: 62
<212> TYPE: DNA
<213> ORGANISM: Artificial
<220> FEATURE:
<223> OTHER INFORMATION: mutant

<400> SEQUENCE: 36
tttagaggcc atatgcatgt ctatcccccc cgaggtcaag ttcaacaaac ccctttgtct      60
tt                                                                    62

<210> SEQ ID NO 37
<211> LENGTH: 9
<212> TYPE: PRT
<213> ORGANISM: Homo sapiens

<400> SEQUENCE: 37

Ala Ile Pro Arg Ser Ile Pro Pro Glu
1               5

<210> SEQ ID NO 38
<211> LENGTH: 9
<212> TYPE: PRT
<213> ORGANISM: Artificial
<220> FEATURE:
<223> OTHER INFORMATION: synthetic peptide

<400> SEQUENCE: 38

Ala Ile Pro Val Ser Ile Pro Pro Glu
1               5

<210> SEQ ID NO 39
<211> LENGTH: 9
<212> TYPE: PRT
<213> ORGANISM: Artificial
<220> FEATURE:
<223> OTHER INFORMATION: syntehtic peptide

```
<400> SEQUENCE: 39

Ala Ile Pro Val Ser Ile Pro Pro Glu
1               5

<210> SEQ ID NO 40
<211> LENGTH: 9
<212> TYPE: PRT
<213> ORGANISM: Artificial
<220> FEATURE:
<223> OTHER INFORMATION: synthetic peptide

<400> SEQUENCE: 40

Ala Ile Pro Leu Ser Ile Pro Pro Glu
1               5

<210> SEQ ID NO 41
<211> LENGTH: 9
<212> TYPE: PRT
<213> ORGANISM: Artificial
<220> FEATURE:
<223> OTHER INFORMATION: synthetic peptide

<400> SEQUENCE: 41

Ala Ile Cys Met Ser Ile Pro Pro Glu
1               5

<210> SEQ ID NO 42
<211> LENGTH: 9
<212> TYPE: PRT
<213> ORGANISM: Artificial Sequence
<220> FEATURE:
<223> OTHER INFORMATION: syntehtic peptide

<400> SEQUENCE: 42

Ala Ile Pro Ala Ser Ile Pro Pro Glu
1               5

<210> SEQ ID NO 43
<211> LENGTH: 9
<212> TYPE: PRT
<213> ORGANISM: Artificial
<220> FEATURE:
<223> OTHER INFORMATION: synthetic peptide

<400> SEQUENCE: 43

Ala Ile Pro Met Ser Ile Pro Pro Lys
1               5

<210> SEQ ID NO 44
<211> LENGTH: 9
<212> TYPE: PRT
<213> ORGANISM: Artificial
<220> FEATURE:
<223> OTHER INFORMATION: synthetic peptide

<400> SEQUENCE: 44

Ala Ala Gly Arg Ser Leu Asn Pro Glu
1               5

<210> SEQ ID NO 45
<211> LENGTH: 9
<212> TYPE: PRT
<213> ORGANISM: Artificial
<220> FEATURE:
<223> OTHER INFORMATION: synthetic peptide

<400> SEQUENCE: 45
```

```
Ile Ala Gly Arg Ser Leu Asn Pro Asn
1               5

<210> SEQ ID NO 46
<211> LENGTH: 9
<212> TYPE: PRT
<213> ORGANISM: Artificial
<220> FEATURE:
<223> OTHER INFORMATION: synthetic peptide

<400> SEQUENCE: 46

Ile Ala Gly Arg Leu Leu Asn Pro Asn
1               5

<210> SEQ ID NO 47
<211> LENGTH: 650
<212> TYPE: PRT
<213> ORGANISM: Artificial
<220> FEATURE:
<223> OTHER INFORMATION: Fc-AAT with leader sequence without linker

<400> SEQUENCE: 47

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
```

```
                    275                 280                 285
Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Glu Pro Lys Ser Cys Asp Lys Thr His Thr Cys Pro Pro Cys
            420                 425                 430

Pro Ala Pro Glu Leu Leu Gly Gly Pro Ser Val Phe Leu Phe Pro Pro
        435                 440                 445

Lys Pro Lys Asp Thr Leu Met Ile Ser Arg Thr Pro Glu Val Thr Cys
450                 455                 460

Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
                485                 490                 495

Glu Gln Tyr Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
        515                 520                 525

Lys Ala Leu Pro Ala Pro Ile Glu Lys Thr Ile Ser Lys Ala Lys Gly
530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Lys Leu Thr Val Asp Lys Ser Arg Trp Gln Gln Gly Asn
    610                 615                 620

Val Phe Ser Cys Ser Val Met His Glu Ala Leu His Asn His Tyr Thr
625                 630                 635                 640

Gln Lys Ser Leu Ser Leu Ser Pro Gly Lys
                645                 650
```

<210> SEQ ID NO 48
<211> LENGTH: 628
<212> TYPE: PRT
<213> ORGANISM: Artificial
<220> FEATURE:
<223> OTHER INFORMATION: Fc-AAT fusion polypeptide with linker without leader sequence

```
<220> FEATURE:
<221> NAME/KEY: linker between immune molecule and AAT
<222> LOCATION: (395)..(396)

<400> SEQUENCE: 48

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Thr Arg Glu Pro Lys Ser
```

```
                385                 390                 395                 400
Cys Asp Lys Thr His Thr Cys Pro Pro Cys Pro Ala Pro Glu Leu Leu
                405                 410                 415

Gly Gly Pro Ser Val Phe Leu Phe Pro Pro Lys Pro Lys Asp Thr Leu
                420                 425                 430

Met Ile Ser Arg Thr Pro Glu Val Thr Cys Val Val Val Asp Val Ser
                435                 440                 445

His Glu Asp Pro Glu Val Lys Phe Asn Trp Tyr Val Asp Gly Val Glu
            450                 455                 460

Val His Asn Ala Lys Thr Lys Pro Arg Glu Glu Gln Tyr Asn Ser Thr
465                 470                 475                 480

Tyr Arg Val Val Ser Val Leu Thr Val Leu His Gln Asp Trp Leu Asn
                485                 490                 495

Gly Lys Glu Tyr Lys Cys Lys Val Ser Asn Lys Ala Leu Pro Ala Pro
                500                 505                 510

Ile Glu Lys Thr Ile Ser Lys Ala Lys Gly Gln Pro Arg Glu Pro Gln
                515                 520                 525

Val Tyr Thr Leu Pro Pro Ser Arg Asp Glu Leu Thr Lys Asn Gln Val
                530                 535                 540

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
                565                 570                 575

Pro Val Leu Asp Ser Asp Gly Ser Phe Phe Leu Tyr Ser Lys Leu Thr
                580                 585                 590

Val Asp Lys Ser Arg Trp Gln Gln Gly Asn Val Phe Ser Cys Ser Val
                595                 600                 605

Met His Glu Ala Leu His Asn His Tyr Thr Gln Lys Ser Leu Ser Leu
                610                 615                 620

Ser Pro Gly Lys
625

<210> SEQ ID NO 49
<211> LENGTH: 626
<212> TYPE: PRT
<213> ORGANISM: Artificial
<220> FEATURE:
<223> OTHER INFORMATION: Fc-AAT fusion polypeptide without linker or
      leader sequence

<400> SEQUENCE: 49

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110
```

```
Thr Thr Gly Asn Gly Leu Phe Leu Ser Glu Gly Leu Lys Leu Val Asp
            115                 120                 125
Lys Phe Leu Glu Asp Val Lys Lys Leu Tyr His Ser Glu Ala Phe Thr
130                 135                 140
Val Asn Phe Gly Asp Thr Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
            180                 185                 190
Lys Trp Glu Arg Pro Phe Glu Val Lys Asp Thr Glu Glu Glu Asp Phe
            195                 200                 205
His Val Asp Gln Ala Thr Thr Val Lys Val Pro Met Met Lys Arg Leu
            210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
            275                 280                 285
Pro Lys Leu Ser Ile Thr Gly Thr Tyr Asp Leu Lys Ser Val Leu Gly
            290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
            355                 360                 365
Pro Phe Val Phe Leu Met Ile Glu Gln Asn Thr Lys Ser Pro Leu Phe
            370                 375                 380
Met Gly Lys Val Val Asn Pro Thr Gln Lys Glu Pro Lys Ser Cys Asp
385                 390                 395                 400
Lys Thr His Thr Cys Pro Pro Cys Pro Ala Pro Glu Leu Leu Gly Gly
                405                 410                 415
Pro Ser Val Phe Leu Phe Pro Pro Lys Pro Lys Asp Thr Leu Met Ile
            420                 425                 430
Ser Arg Thr Pro Glu Val Thr Cys Val Val Val Asp Val Ser His Glu
            435                 440                 445
Asp Pro Glu Val Lys Phe Asn Trp Tyr Val Asp Gly Val Glu Val His
            450                 455                 460
Asn Ala Lys Thr Lys Pro Arg Glu Glu Gln Tyr Asn Ser Thr Tyr Arg
465                 470                 475                 480
Val Val Ser Val Leu Thr Val Leu His Gln Asp Trp Leu Asn Gly Lys
                485                 490                 495
Glu Tyr Lys Cys Lys Val Ser Asn Lys Ala Leu Pro Ala Pro Ile Glu
            500                 505                 510
Lys Thr Ile Ser Lys Ala Lys Gly Gln Pro Arg Glu Pro Gln Val Tyr
            515                 520                 525
Thr Leu Pro Pro Ser Arg Asp Glu Leu Thr Lys Asn Gln Val Ser Leu
```

535                 540
Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
610                 615                 620

Gly Lys
625

<210> SEQ ID NO 50
<211> LENGTH: 1887
<212> TYPE: DNA
<213> ORGANISM: Artificial
<220> FEATURE:
<223> OTHER INFORMATION: cDNA for Fc-AAT with linker without leader
      sequence

<400> SEQUENCE: 50
gaggatcccc agggagatgc tgcccagaag acagatacat cccaccacga tcaggatcac     60
ccaaccttca acaagatcac ccccaacctg gctgagttcg ccttcagcct ataccgccag    120
ctggcacacc agtccaacag caccaatatc ttcttctccc cagtgagcat cgctacagcc    180
tttgcaatgc tctccctggg gaccaaggct gacactcacg atgaaatcct ggagggcctg    240
aatttcaacc tcacggagat tccggaggct cagatccatg aaggcttcca ggaactcctc    300
cgtaccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca agaaacagat caacgattac    480
gtggagaagg gtactcaagg gaaaattgtg gatttggtca aggagcttga cagagacaca    540 gttttttgctc tggtgaatta catcttcttt aaaggcaaat gggagagacc ctttgaagtc    600
aaggacaccg aggaagagga cttccacgtg gaccaggcga ccaccgtgaa ggtgcctatg    660
atgaagcgtt taggcatgtt taacatccag cactgtaaga gctgtccagc tgggtgctg     720 ctgatgaaat acctgggcaa tgccaccgcc atcttcttcc tgcctgatga ggggaaacta    780
cagcacctgg aaaatgaact cacccacgat atcatcacca gttcctgga aaatgaagac    840 agaaggtctg ccagcttaca tttacccaaa ctgtccatta ctggaaccta tgatctgaag    900
agcgtcctgg gtcaactggg catcactaag gtcttcagca atgggctga cctctccggg    960 gtcacagagg aggcaccct gaagctctcc aaggccgtgc ataagctgt gctgaccatc   1020 gacgagaaag ggactgaagc tgctggggcc atgttttag aggccatacc catgtctatc   1080 cccccgagg tcaagttcaa caaacccttt gtcttcttaa tgattgaaca aaataccaag   1140
tctcccctct tcatgggaaa agtggtgaat cccacccaaa aaacgcgtga gcccaaatct   1200
tgtgacaaaa ctcacacatg cccaccgtgc ccagcacctg aactcctggg gggaccgtca   1260
gtcttcctct tccccccaaa acccaaggac accctcatga tctcccggac ccctgaggtc   1320
acatgcgtgg tggtggacgt gagccacgaa gaccctgagg tcaagttcaa ctggtacgtg   1380
gacggcgtgg aggtgcataa tgccaagaca aagccgcggg aggagcagta caacagcacg   1440

| | |
|---|---|
| taccgtgtgg tcagcgtcct caccgtcctg caccaggact ggctgaatgg caaggagtac | 1500 |
| aagtgcaagg tctccaacaa agccctccca gcccccatcg agaaaaccat ctccaaagcc | 1560 |
| aaagggcagc cccgagaacc acaggtgtac accctgcccc catcccggga tgagctgacc | 1620 |
| aagaaccagg tcagcctgac ctgcctggtc aaaggcttct atcccagcga catcgccgtg | 1680 |
| gagtgggaga gcaatgggca gccggagaac aactacaaga ccacgcctcc cgtgctggac | 1740 |
| tccgacggct ccttcttcct ctacagcaag ctcaccgtgg acaagagcag gtggcagcag | 1800 |
| gggaacgtct tctcatgctc cgtgatgcat gaggctctgc acaaccacta cacgcagaag | 1860 |
| agcctctccc tgtctccggg taaatga | 1887 |

```
<210> SEQ ID NO 51
<211> LENGTH: 1959
<212> TYPE: DNA
<213> ORGANISM: Artificial
<220> FEATURE:
<223> OTHER INFORMATION: cDNA for Fc-AAT with linker and leader sequence

<400> SEQUENCE: 51
```

| | |
|---|---|
| atgccgtctt ctgtctcgtg gggcatcctc ctgctggcag gcctgtgctg cctggtccct | 60 |
| gtctccctgg ctgaggatcc ccagggagat gctgcccaga gacagataca tcccaccac | 120 |
| gatcaggatc acccaacctt caacaagatc acccccaacc tggctgagtt cgccttcagc | 180 |
| ctataccgcc agctggcaca ccagtccaac agcaccaata tcttcttctc cccagtgagc | 240 |
| atcgctacag cctttgcaat gctctccctg gggaccaagg ctgacactca cgatgaaatc | 300 |
| ctggagggcc tgaatttcaa cctcacggag attccgaggg ctcagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ttgtaccact cagaagcctt cactgtcaac ttcggggaca ccgaagaggc caagaaacag | 540 |
| atcaacgatt acgtggagaa gggtactcaa gggaaaattg tggatttggt caaggagctt | 600 |
| gacagagaca cagttttgc tctggtgaat tacatcttct ttaaaggcaa atgggagaga | 660 |
| cccttgaag tcaaggacac cgaggaagag gacttccacg tggaccaggc gaccaccgtg | 720 |
| aaggtgccta tgatgaagcg tttaggcatg tttaacatcc agcactgtaa gaagctgtcc | 780 |
| agctgggtgc tgctgatgaa atacctgggc aatgccaccg ccatcttctt cctgcctgat | 840 |
| gaggggaaac tacagcacct ggaaaatgaa ctcacccacg atatcatcac caagttcctg | 900 |
| gaaaatgaag acagaaggtc tgccagctta catttaccca aactgtccat tactggaacc | 960 |
| tatgatctga agagcgtcct gggtcaactg ggcatcacta aggtcttcag caatgggcct | 1020 |
| gacctctccg gggtcacaga ggaggcaccc ctgaagctct ccaaggccgt gcataaggct | 1080 |
| gtgctgacca tcgacgagaa agggactgaa gctgctgggg ccatgttttt agaggccata | 1140 |
| cccatgtcta tcccccccga ggtcaagttc aacaaaccct tgtcttctt aatgattgaa | 1200 |
| caaaatacca agtctcccct cttcatggga aaagtggtga atcccaccca aaaaacgcgt | 1260 |
| gagcccaaat cttgtgacaa aactcacaca tgcccaccgt gcccagcacc tgaactcctg | 1320 |
| gggggaccgt cagtcttcct cttccccca aaacccaagg acaccctcat gatctcccgg | 1380 |
| acccctgagg tcacatgcgt ggtggtggac gtgagccacg aagaccctga ggtcaagttc | 1440 |
| aactggtacg tggacggcgt ggaggtgcat aatgccaaga caaagccgcg ggaggagcag | 1500 |
| tacaacagca cgtaccgtgt ggtcagcgtc ctcaccgtcc tgcaccagga ctggctgaat | 1560 |
| ggcaaggagt acaagtgcaa ggtctccaac aaagccctcc cagcccccat cgagaaaacc | 1620 |

```
atctccaaag ccaaagggca gccccgagaa ccacaggtgt acaccctgcc cccatcccgg    1680
gatgagctga ccaagaacca ggtcagcctg acctgcctgg tcaaaggctt ctatcccagc    1740
gacatcgccg tggagtggga gagcaatggg cagccggaga acaactacaa gaccacgcct    1800
cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggtaaatga                           1959
```

COMPOSITIONS, METHODS AND USES FOR ALPHA-1 ANTITRYPSIN FUSION MOLECULES

PRIORITY

This PCT application claims priority to U.S. Provisional application No. 61/500,795 filed on Jun. 24, 2011. This application is incorporated herein by reference in its entirety for all purposes.

FIELD

Embodiments herein relate to compositions of recombinant alpha-1 antitrypsin (α-1 antitrypsin, AAT). In certain embodiments, recombinant AAT disclosed herein can be more readily purified than other forms of AAT. In other embodiments, recombinant AAT has enhanced anti-inflammatory and anti-immune activities compared to naturally-occurring AAT or other commercial formulations of AAT. In yet other embodiments, 2-fold, 10-fold or 100 fold less recombinant AAT (rAAT) may be used in the place of any and all current forms of plasma-derived AAT for prevention or treatments of a condition or disease in a subject. In some embodiments, rAAT can be used to treat a subject having a condition such as inflammation of various tissues or organs, infections or other health conditions.

BACKGROUND

AAT

Normal plasma concentration of alpha-1 antitrypsin (AAT) ranges from 1.3 to 3.5 mg/ml. Under certain conditions, AAT easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen.

SUMMARY

Embodiments herein report generating and using recombinant constructs of alpha-1 antitrypsin having superior properties to commercially available AAT compositions. Other embodiments report methods for purifying and scaling-up recombinant AAT production for therapeutic uses. In accordance with these embodiments, recombinant AAT can be isolated for use for any AAT-related activity, for example, as an anti-inflammatory agent, an immune modulator and/or a serine protease inhibitor.

In certain embodiments, recombinant AAT disclosed herein includes a full length molecule or carboxyterminal peptide derivative thereof generated by any recombinant technology known in the art. Some embodiments concern constructs including AAT or a carboxyterminal derivative thereof having immunological elements associated with AAT, for example, to use for rapid purification and activity conservation of the AAT or to increase activity of AAT or its peptides. Other embodiments concern simultaneous synthesis of more than one constructs having AAT molecules each associated with an immunological element (e.g., an Fc fragment) and co-purified as a unit. Other embodiments can concern generating a construct of one or more carboxyterminal derivative(s) or fragment(s) of AAT including, for example, a fragment of the last 80 AAs (on the carboxyterminus) or subfragments thereof (e.g., about 40, abut 30, about 20 or about 10 AAs, or about 5 AAs) of the molecule associated with one or more immune molecule to form a construct for compositions, methods and uses disclosed herein.

An AAT molecule of a construct contemplated herein can concern naturally occurring alpha-1 antitrypsin (e.g., human) or the most abundant form of AAT or other naturally-occurring form thereof, or fragments, or derivatives thereof, or mutant forms of AAT having no significant serine protease inhibitor activity, or alleles thereof (for example, there are approximately 100 naturally occurring AAT variants and any of these variants can be used in constructs disclosed herein), or analogs thereof or fusion protein thereof (e.g., a human IgG or fragment of human IgG). In accordance with these embodiments, a final construct or fusion polpeptide may include 2 AAT molecules or fusion polypeptides each associated with a common immunological fragment (e.g., an Fc fragment) wherein the AAT-immune fragment constructs are linked together by disulfide bonds to form a dimer AAT-immune fragment fusion molecule (See for example, FIG. 2A and FIGS. 6A-6B).

In certain methods disclosed herein, purification of the AAT or AAT-peptide associated with the immune molecule significantly increases activity of an AAT composition compared to commercially available formulations or native AAT. In addition, time to purification is dramatically reduced by eliminating multiple purification steps while preserving critical activities of the constructs or fusion molecules. In other embodiments, improved recovery of a fusion molecule contemplated herein can be more readily achieved using linker molecules between the AAT molecule and the immune fragment. Certain fusion molecules disclosed herein are capable of inhibiting cytokines or modulate the immune and inflammatory functions of the molecules compared to controls (e.g., typical purification of naturally occurring AAT and purification of commercially available formulas). In accordance with these embodiments, a unit including two or more AAT-immune constructs (or AAT fragments) can be purified and used in compositions and methods disclosed herein. Fc-huAAT can be used in any method or composition contemplated herein. Other embodiments include using IgG1, IgG2 IgG3, IgG4 or IGD Fc fragments linked to an AAT molecule purified by rapid purification methods in order to preserve activity of the AAT molecule. For example, certain embodiments disclosed herein concern using Protein A as minimum step (e.g., one-step) purification in order to avoid the deleterious effects of other methods known in the art. Some embodiments herein concern preserving 85%, 90%, 95% or more anti-inflammatory activity compared to standard purifications used for commercially available products (e.g., Aralast™, Prolastin™) and/or compared to naturally occurring AAT found in blood plasma. In one embodiment, recombinant molecules of the instant application have demonstrated 2 to 10, 10 to 100, and in certain embodiments 2 to 100 fold more activity compared to commercially available formulations. Disclosed herein are methods to create and recover constructs having acitivities similar to and in certain embodiments, superior to in vivo or native AAT. Certain activities known to be of interest regarding AAT include, but are not limited to, immunomodulatory or inflammatory modulation activities. For example, fusion molecules described herein can behave as anti-inflammatory molecules due to induction of naturally occurring anti-inflammatory molecules such as the IL-1 receptor antagonist (IL-1Ra), CTLA-4, IL-18 binding protein and/or IL-10 and the like. It is contemplated herein that constructs described can be isolated and assessed for activities that can be other than serine protease inhibitor activities. In some embodiments, constructs disclosed herein have greater IL-1 receptor antagonist activity compared to commercially available compositions.

In certain embodiments, compositions (e.g., construct or fusion polypeptide compositions) and methods concern modulating adverse effects of radiation on a subject. In some embodiments, compositions and methods concern treating a subject having radiation therapy or radiation for example, when administered to a subject having cancer or suspected of developing a malignancy or for uncontrolled cellular growth. Other embodiments disclosed herein concern treating a subject having been exposed to radiation, for example, by accident or by a purposeful act.

In other embodiments, a composition disclosed herein can be administered to a subject every time a subject undergoes radiation and/or chemotherapy. Some embodiments disclosed herein concern treatment of a subject undergoing cancer therapies. Cancer treatments include, but are not limited to, treatment for bladder, breast, kidney, leukemia, lung, myeloma, liposarcoma, lymphoma, tongue, prostate, stomach, colon, uterine cancers, melanoma, pancreatic, eye and other known cancers.

Some embodiments disclosed herein concern treating a subject having prostate cancer. In accordance with these embodiments, a male subject having prostate cancer can be treated with compositions disclosed herein before, during or after radiation and/or chemotherapy in order to reduce development of impotence or erectile dysfunction, common side effects of prostate cancer therapies.

Other embodiments concern combination therapies for the treatment of a subject undergoing cancer related therapies, for example a composition disclosed herein can be combined with any other agent known to shrink or eliminate a tumor or reduce metastasis of a tumor in the subject or treat other aspects of cancer in the subject.

In certain embodiments, treating the subject with a composition encompassed herein to modulate normal cell damage can be by at least 10%, or by at least 20% or by at least 30%, or by at least 40%, or by at least 50%, or by at least 60%, or by at least 70%, or by at least 80%, or by at least 90% compared to a subject not treated with the composition.

Some embodiments concern administering AAT generated by using recombinant technology to a subject in need of AAT therapy. In accordance to these embodiments, a subject could have an AAT-deficiency, an inflammatory or immune condition or other AAT-related condition known in the art. Certain embodiments herein include administering a composition having at least one construct and a pharmaceutically acceptable carrier to a subject in need of such a treatment. In certain embodiments, doses administered to a subject can include a 2-fold, 10-fold or 100-fold reduction in dose to the subject compared to commercially available formulations. In certain embodiments, a dose can be about 0.01 mg/kg, 0.1 mg/kg to about 10 mg/kg to a subject compared to 10 mg/kg to 100 mg/kg (concentrations of commonly used commercially available AAT such as Aralast™ or Prolastin C™).

Some embodiments of the present invention report modulating the onset or progression of cardiac tissue remodeling (e.g., enlargement and necrosis of cardiac tissue), for example, left or right ventricular (LV) remodeling. In accordance with these embodiments, intervention for example, by administering a composition disclosed herein, can modulate onset, severity (e.g., of damage) or progression before, during, or after a cardiac event that can lead to heart muscle damage. In yet other embodiment, compositions disclosed herein can be administered to a subject having a heart condition to reduce early or late infarct size. In accordance with these embodiments, an early infarct can be one measured before (for example, a baseline), during or within 48 hours after surgery or other cardiac event. In other embodiments, a late infarct can be one measured after 48 hours or up to days or weeks after surgery or other cardiac event, for example 7 days after a cardiac event. In yet other embodiments, compositions disclosed herein can be used to treat a subject having a cardiac event (e.g., myocardial infarction), to modulate cardiac enlargement and dysfunction as a consequence of the cardiac event by about 5%, or about 10%, or about 15%, or about 20% or about 25%, or about 30% or more compared to a subject not treated with these compositions.

Certain embodiments concern compositions for treating a subject having a cardiac event. In accordance with these embodiments, a composition can include, recombinant alpha-1 antitrypsin (e.g., human), or fusion proteins or peptides thereof or recombinants, or mutants thereof having no significant serine protease inhibitor activity, or alleles thereof (for example, there are approximately 100 naturally occurring AAT varients), or analogs thereof or fusion proteins thereof (e.g., a human IgG or fragment of human IgG (Fc)). Some embodiments concern administering naturally occurring AAT to a subject having or having had a cardiac event in order to modulate LV remodeling. Other embodiments can concern administering a composition of one or more carboxyterminal derivative(s) or fragment(s) of AAT including, for example, a fragment of the last 80 AAs of the 394 AA naturally occurring AAT (SEQ ID NO. 1 and 33). Certain embodiments concern treating a subject having a cardiac condition with a recombinantly-produced fusion AAT peptide disclosed herein in order to ameliorate the cardiac condition.

Other embodiments include treating a subject having an infection (e.g., bacteria or viral infection) or preventing a subject from getting an infection using compositions disclosed herein.

Some embodiments concern compositions disclosed herein to reduce or prevent graft rejection. In other embodiments, compositions disclosed herein can be used to reduce the incidence or prevent Graft versus Host disease (GVHD). In other embodiments, compositions disclosed herein can be used to reduce cellular transplant rejections or side effects thereof. Cellular transplantation can include islet cell, stem cell, corneal epithelial cells, liver cells, skin or other similar transplantation. Some embodiments concern reducing inflammatory activity and/or adverse immune responses in a subject undergoing a transplant.

Other embodiments herein concern treating a subject with an autoimmune disorder in order to treat the condition and/or inhibit detrimental immune responses in the subject.

In certain embodiments, compositions for administration can be in a range of between about 0.1 ng and about 10 mg per ml or mg of the formulation. A therapeutically effective amount of AAT peptides or constructs that have similar activities as AAT or peptides may be measured in molar concentrations and may range between about 1 nM and about 10 mM. The formulation is also contemplated in combination with a pharmaceutically or cosmetically acceptable carrier. Precise doses can be established by well known routine clinical trials without undue experimentation. In one embodiment, a subject may be treated for a conditions with a single dose (e.g., 0.6 mg/kg to 0.8 mg/kg by IV infusion depending on the potency of the construct composition compared to a control) of an active agent (e.g., AAT construct or AAT peptide derivative thereof). In accordance with this embodiment, the subject can be treated with follow-on treatments (e.g., 5 to 10 days following a single dose or more) as determined by a health professional. Other embodiments can include using a control population having a placebo (e.g., human serum albumin administration or other comparable placebo) and comparing a placebo effect to a population receiving compositions disclosed herein.

Any method for administering a composition disclosed herein is contemplated. In certain embodiments, a composition can be administered to a subject in need thereof intravenously, intranasally, subcutaneously, orally, by inhalation, applied to the skin e.g., topically, by suppository, vaginally or by any method known in the art.

In certain embodiments, the subject is a mammal. In some embodiments, the mammal is a human. In yet other embodiments, the subject is a pregnant female or young child. In other embodiments, the subject is a pet, a domesticated animal or livestock.

In other embodiments, the subject or mammal can be a non-domesticated mammal such as a captive or free wild animal.

In certain embodiments, compositions comprising human AAT mutants may have no significant serine protease inhibitor activity can be used in constructs disclosed herein for use in methods described (e.g., AAT fusion peptide derivative or Reactive Center Loop (RCL) related mutant fusion polypeptide). In accordance with these embodiments, recombinant molecules or fusion protein constructs disclosed herein have no significant serine protease inhibition activity. These constructs can be generated where they associate with an immune molecule (e.g., Fc). For example, fusion with an immune molecule can provide a convenient way for rapid purification of a fusion polypeptide thereby preserving activities of the AAT or carboxyterminal thereof by reducing purification steps. In certain embodiments, the purification step is a single step using an affinity process (e.g., Protein A). These processes preserve conformation of the constructs disclosed herein by reducing deleterious purification steps used in other commercially available formulations (e.g., Aralast™, Prolastin C™). Other embodiments concern AAT-derived fragment constructs adapted to have no significant serine protease inhibitor activity. Other constructs herein can include, but are not limited to, constructs including a carboxy-terminal peptide or amino-terminal peptides corresponding to AAT, an analog thereof, any derivative of AAT carboxy terminus that binds to serpin-enzyme complex (SEC) receptor or a combination thereof linked to an immune molecule (e.g., IgG molecule).

Pharmaceutical compositions contemplated herein may further include an agent selected from the group consisting of an anti-inflammatory agent, an immunosuppressive agent, an immunomodulatory agent, an anti-viral agent, an anti-pathogenic agent, an anti-bacterial agent, a protease inhibitor, and a combination thereof depending on need of the subject. Some of these agents include, but are not limited to, one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, T-cell-proteins; and calcipotriols; Celcept®, mycophenolate mofetil, and analogues thereof taken either alone or in combination.

As such, those skilled in the art will appreciate that the conception, upon which this disclosure is based, can readily be used as a basis for designing other methods for carrying out the several features and advantages of embodiments of the present invention.

BRIEF DESCRIPTION OF THE DRAWINGS

The following drawings form part of the present specification and are included to further demonstrate certain embodiments disclosed herein. Embodiments may be better understood by reference to one or more of these drawings in combination with the detailed description of specific embodiments presented herein.

DESCRIPTION OF ILLUSTRATIVE EMBODIMENTS

Definitions

Figure 1:
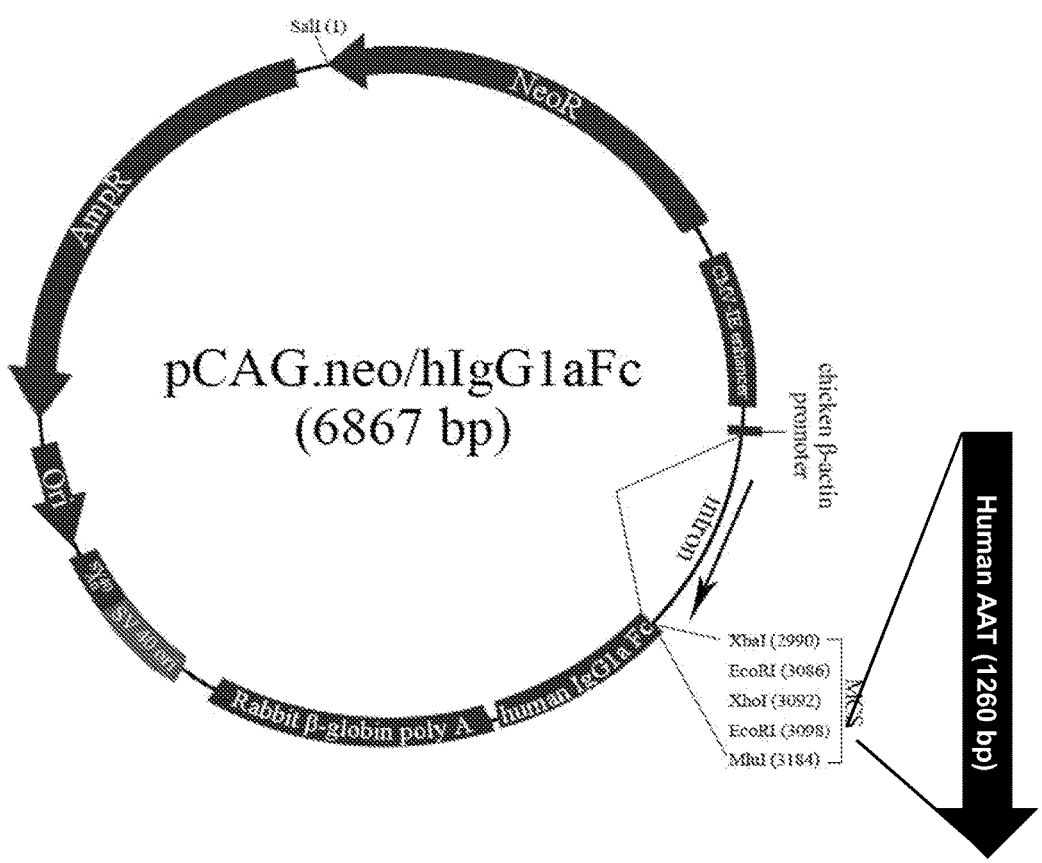
FIG. 1 represents a schematic of an AAT construct contemplated of use for some embodiments disclosed herein.

As used herein, "a" or "an" may mean one or more than one of an item.

As used herein, "about" can mean plus or minus 10%, for example, about 10 minutes can mean from 9 to 11 minutes.

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

It has been traditionally thought that AAT (alpha-1 antitrypsin) anti-inflammatory activities were attributed to its ability to inhibit serine proteases, and particularly neutrophil elastase. This is the basis for its use in replacement therapy for humans with AAT deficiencies. AAT that is currently commercially available for human use is standardized by its anti-elastase units not for other AAT-related activities. These commercially available formulations are purified from pooled human plasma, but these are not pure (although some are purer than others) because they contain other human serum proteins. The majority of studies on human AAT in vitro as well as in vivo models depend on the use of these commercially available preparations directed to serine protease inhibition activity, each approved for use in humans. Although infusions of AAT in humans with various AAT deficiency states are considered safe, the role of contaminating proteins remains unknown. Certain embodiments herein report quick production of recombinant forms of AAT of high purity and high activity to overcome issues of contaminating co-purified plasma proteins.

Excess inflammation or inflammation activation can result in the initiation, progression and destructive nature of several chronic diseases, for example chronic destructive or wasting diseases. These include, but are not limited to, autoimmune diseases, such as rheumatoid arthritis, diabetes such as Type 1 where insulin-producing beta cells can be destroyed by an immune attack. Other conditions that may be treated by compositions and methods disclosed herein include Type 2 diabetes. In addition to autoimmune diseases, chronic inflammation of coronary arteries can increase the risk of a heart attack or stroke. Chronic inflammation also contributes to inflammation in the intestines (e.g., Crohn's Disease, inflammatory bowel disease (IBD) or ulcerative colitis). Several naturally occurring proteins are produced each day in a subject that control inflammation in the subject. AAT is one of these proteins. One drawback of a therapy with AAT is that commercially available AAT is isolated from the plasma of human blood donors therefore supply is limited to available plasma. Uses of therapeutic AAT are growing because its application is not limited to the current uses such as chronic pulmonary obstructive disease (COPD) and AAT replacement therapies.

One drawback of a therapy with AAT is that commercially available AAT is isolated from the plasma of human blood donors therefore supply is limited to available plasma. Uses of therapeutic AAT are growing because its application is not limited to the current uses such as chronic pulmonary obstructive disease, emphysema, cystic fibrosis, bronchiocytis, pulmonary fibrosis, and AAT replacement therapies.

In certain embodiments, Fc molecules may be associated with AAT molecules to make dimers of Fc-AAT, for example, linked by disulfide bonds through the immune molecule. In other embodiments, monomeric molecules of Fc-AAT can be generated and used in methods disclosed herein. Any of the molecules described herein can be rapidly purified using, for example, Protein A column, other affinity purification methods or matrix or other quick purification or enrichment method for rapid separation to preserve activity.

Embodiments herein report generating constructs of alpha-1 antitrypsin (AAT) or carboxyterminal fragment thereof having superior properties to current commercially available AAT compositions. Other embodiments report methods for rapidly purifying fusion proteins or peptides and subsequent uses for purified AAT fusion molecules disclosed herein. It is contemplated that commercially available AAT derived from blood plasma is in short supply, is currently purified by methods that destroy important properties of AAT and a need exists for synthetic versions of this molecule or updated purification methods where the synthetically produced AATs are capable of performing as well if not better than native forms of AAT or AAT derived peptides.

With respect to AAT activities other than serine protease inhibition, AAT exerts anti-inflammatory properties by several mechanisms. Preliminary data using a mutation of the anti-protease site (e.g., to reduce anti-protease activity to insignificant levels) support the concept that some of AAT's activities do not require the anti-protease properties of AAT. In certain embodiments, different recombinant truncated and mutant forms of naturally occurring human AAT (e.g., 394 AA, $M_r$ about 51,000 or other AAT formulations) are generated in order to assess anti-inflammatory properties of the molecule. This approach allows for producing AAT molecules of various compositions, which is extremely difficult using the standard methods of plasma-derived AAT. It was demonstrated that anti-inflammatory properties of AAT can be oxidized by currently used purification procedures of commercially available compositions thus, the instant methods for preparing and purifying fusion molecules of AAT are superior to the current methods. Methods disclosed herein provide superior rapid purification methods for preserving AAT-related activities in fusion molecules and constructs described herein.

In certain previously disclosed methods, it has been demonstrated that AAT blocks toxic activities of IL-1β on mouse model and human pancreatic islet cells. Some embodiments herein concern testing and verifying whether fusion molecules or recombinant production of AAT fusion molecules are capable of mimicking this activity. In certain embodiments, recombinantly-produced fusion peptides of the carboxyl terminal region of human AAT are generated for blocking toxic activities or production of IL-1β and for reducing caspase-1 activity. These fusion peptides are useful for blocking or reducing production of or activities of pro-inflammatory molecules and therefore are useful for treatment and prevention of many health conditions related to uncontrolled inflammatory responses.

AAT was first classified as a protease inhibitor belonging to the serpin superfamily. It is generally known as serum trypsin inhibitor. AAT can also be referred to as alpha-1 proteinase inhibitor (A1PI) because it inhibits a wide variety of proteases. AAT protects tissues from enzymes of inflammatory cells, such as neutrophil elastase, and typically has a range in blood of about 1.5 to 3.5 gram/liter. Over 100 different variants of $\alpha_1$-antitrypsin have been described in various populations. The most common variety of AAT is termed M, based on its migration in an IEF gel. Other variants are termed A-L and N-Z, depending on whether they run proximal or distal to the M band. The presence of deviant bands on IEF can signify the presence of AAT deficiency. As indicated above, M type AAT has several subtypes and all of these subtypes are contemplated of use herein. It is contemplated that any variants of AAT can be used as fusion molecules using construct designs disclosed herein.

The current trend for obtaining therapeutic concentrates of AAT is to prepare AAT from the blood plasma of blood donors (e.g., human donors for example). This is a very limited resource and requires extensive purification steps to get to a marketable product. So far, the United States Food & Drug Administration has approved the use of several commercial products derived from human plasma. For example, some of these products include Prolastin®, ProlastinC®, (Talecris (now Grifols, Raleigh, N.C.)), Zemaira®, and Aralast® (Baxter) and Kamada has both an aerosol and an intravenous product (Kamada, Israel). Most of these formulations are administered intravenously for AAT therapy in AAT deficient patients and can cost up to $100,000 per year per patient. It has been demonstrated that plasma isolated AAT has reduced activity compared to AAT derived from blood. In addition, the current purification protocols result in significantly reduced activity and AAT from the plasma in general. Compositions disclosed herein have increased anti-inflammatory activity similar to that of blood not of plasma-derived AAT; and greater activity than the current commercially available formulations which have activities that are based on anti-protease activities not anti-inflammatory activities.

One study analyzed and compared three of the FDA-approved products in terms of its primary structure and glycosylation. Several of the products showed differences compared to the normal human plasma AAT that are likely introduced during purifications procedures. In addition, it was previously demonstrated that comparison of the commercial formulations in certain studies had large variability regarding serine protease inhibition activity and AAT purity. Recently, one of the standard commercially available formulations, Prolastin®, was evaluated and a new formulation ProlastinC® was purified differently than Prolastin®, in order to increase anti-protease activity (e.g., serine protease inhibition activity) in the final product. All of the activities reported for these commercial products are directed to assessing serine protease inhibition activities not anti-inflammatory or immune modulatory activity or alternative AAT-related activities. Thus, the current commercial products are not only scarce in quantity but are inferior in quality to the naturally-occurring formulations.

In spite of efforts to improve AAT formulations, there is a finite supply of plasma AAT available and therefore recombinant AAT molecules have been sought with little to no success up until now. Recombinant molecules generated previously were sometimes equal to but often less active when assayed by serine protease inhibitor assays compared to the commercially available formulations previously indicated. Thus, limited supply of plasma and inferior recombinant AAT molecules of the past have left a void for generating adequate supplies of AAT for use in previous and recently discovered methodologies.

Some embodiments herein concern generating a highly active, highly functional recombinant AAT construct relative to commercially available formulations for use in any AAT method or treatment known in the art. In certain embodiments, recombinant AAT disclosed herein includes a full length molecule or carboxyterminal peptide derivative thereof. Some embodiments concern simultaneous synthesis of more than one construct having AAT molecules each associated with an immunological element (e.g., an Fc fragment or other fragment linked by a disulfide bond) and co-purified to generate a dimer. Other embodiments can concern generating a construct of one or more carboxyterminal derivative(s) or fragment(s) of AAT including, for example, a fragment of the last 80, 70, 60, 50, 40, 30 amino acids or other fragment of the carboxyterminus of the molecule associated or fused to one or more immune molecule(s) to form a construct for methods and uses disclosed herein.

Figure 6A:
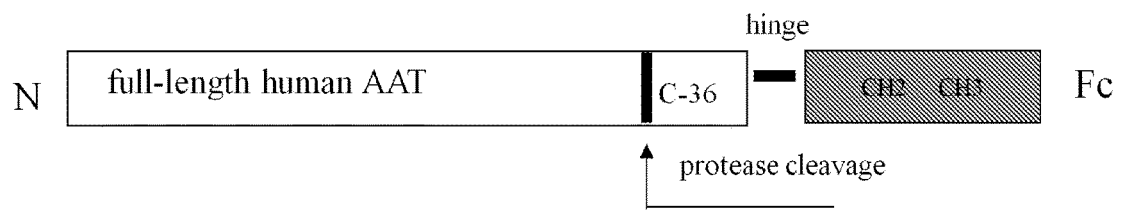
FIGS. 6A-6B represents exemplary constructs contemplated herein.
Figure 6B:
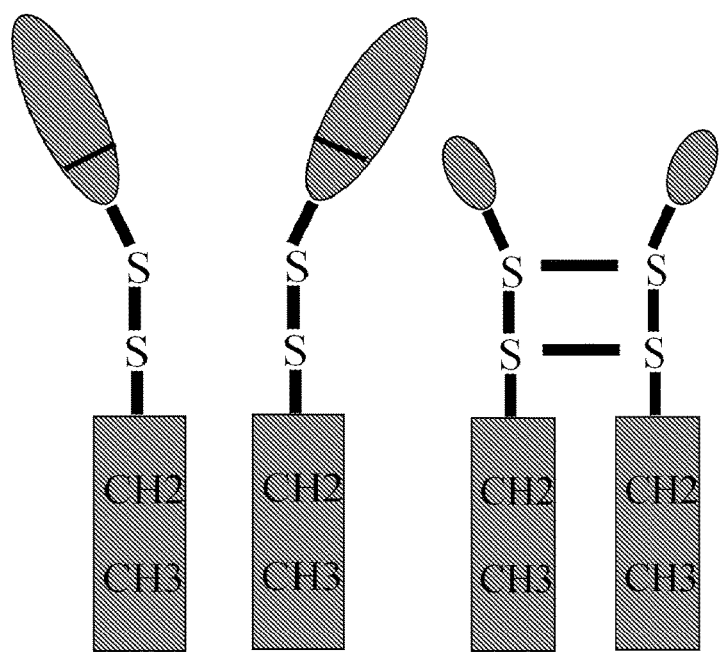

An AAT molecule of a construct contemplated herein can concern naturally occurring alpha-1 antitrypsin (e.g., human or other mammal) in total (or with a signal sequence or other directing sequence), or fragments, or derivatives thereof, or mutant forms of AAT, any AAT molecule having no significant serine protease inhibitor activity, or alleles thereof (for example, there are approximately 100 naturally occurring AAT varients), or analogs thereof or fusion protein thereof (e.g., a human IgG or fragment of human IgG). In accordance with these embodiments, a construct can include dimeric AAT constructs associated with an immunological fragment (e.g., an Fc fragment that links two molecules of AAT) wherein the Fc-AAT constructs are linked together by one or more disulfide bond(s). See for example, FIG. 2A and FIGS. 6A-6B disclosed herein. In certain methods, purification of recombinant AAT or AAT-peptide and immune molecule complexes increase activity of the AAT or AAT-peptide by significantly reducing purification steps and significantly increasing potency of AAT or AAT-peptide. In accordance with these embodiments, recombinant AAT molecules contemplated herein can be used as a fusion polypeptide (e.g., dimer or monomeric form) or can be cleaved from its immune molecule after purification and used as in reduced concentrations compared to commercially available formulations. Some embodiments concern, using ½, ¼, $1/10^{th}$, to $1/100^{th}$ of a concentration compared to commercially available formulations. In certain examples, these molecules can be used in compositions to inhibit cytokines or modulate the immune and inflammatory functions of the molecules compared to controls (e.g., typical purification of naturally occurring AAT and purification of commercially available formulas). In one embodiment, recombinant molecules of the instant application have demonstrated more activity than current commercially available formulation. Certain activities known to be of interest regarding AAT constructs of the instant invention include immunomodulatory or inflammatory modulation activities. In some embodiments, constructs disclosed herein have increased IL-1β receptor antagonist activity compared to commercially available compositions.

In certain embodiments, the subject is a mammal. In some embodiments, the mammal is a human. In yet other embodiments, the subject is a male, a female, a pregnant female, an infant or a juvenile.

Some Uses for Recombinant AAT in the Treatment of Health Conditions

Some embodiments reported herein concern using recombinant AAT or fusion protein or carboxyterminal fragment fusion molecule thereof to treat a subject in need of AAT therapy. AAT treatments have been reported of use in a variety of conditions including, but not limited to, apoptosis related conditions, nitric oxide related conditions, ischemia-reperfusion dysfunction induced conditions, graft rejection and cellular rejection, diabetes, emphysema, other lung conditions, treatment and prevention of bacterial infection, treatment and prevention of viral infections, radiation induced injury and the like.

Some embodiments herein concern compositions of use to treat an inflammatory disorder (e.g., IBD, arthritis) where the composition to treat the condition has reduced or eliminated serine protease activity.

In certain embodiments, compositions and methods disclosed herein can be used to reduce or prevent onset of inflammatory bowel disorder in a subject. In accordance with these embodiments, reduction in conditions associated with IBS in a subject may be on the order of about 10-20%, or about 30-40%, or about 50-60%, or about 75-100% reduction or inhibition. In accordance with these embodiments, a subject having IBS or IBD may be treated with a pharmaceutically acceptable composition of recombinant or a fusion protein of AAT or AAT-carboxyterminal peptide to reduce wasting or to reduce loss of or restore barrier function compared to a control subject not receiving such a composition.

Some embodiments herein concern restoring bowel or intestinal hyperpermeability in a subject having an acute or chronic condition. In accordance with these embodiments bowel or intestinal hyperpermeability or loss of barrier function can be due to chronic diseases such as systemic inflammatory response syndrome (SIRS), inflammatory bowel disease, type 1 diabetes, allergies, and asthma. In certain embodiments, a subject having bowel or intestinal hyperpermeability can be treated by a health professional by a predetermined regimen such as daily, twice weekly, weekly or other predetermined regimen.

In certain embodiments, compositions disclosed herein can be used to treat certain indications including but not limited to diabetes (e.g., Type 1 and Type 2), immune diseases such as autoimmune disease, inflammatory diseases, cardiac disorders infectious disease and others. Some diseases disclosed herein may fall under more than one category such as asthma which can be considered an inflammatory disease, an autoimmune disease or a lung disease or other. In certain embodiments, compositions disclosed herein can be used to treat autoimmune diseases that include, but are not limited to, rheumatic diseases such as rheumatoid arthritis, systemic lupus erythematosus (SLE), Type I diabetes, and autoimmune diseases of the thyroid, gut, and central nervous system (e.g., rheumatoid arthritis, lupus erythematosus, Sjogren's syndrome, scleroderma, mixed connective tissue disease, dermatomyositis, polymyositis, Reiter's syndrome, and Behcet's disease); autoimmune diseases of the central nervous system (e.g., multiple sclerosis, myasthenia gravis, or encephalomyelitis); autoimmune disease of the gastrointestinal system: (e.g., Crohn's disease, ulcerative colitis, inflammatory bowel disease, Celiac disease, Sprue); autoimmune disease of the thyroid: (e.g., Hashimoto's thyroiditis, or Graves' Disease); and ocular autoimmune disease, (e.g., uveitis). Autoimmune disorder contemplated herein, can concern Alopecia greata, nkylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, Bullous pemphigoid, cardiomyopathy, Celiac sprue-dermatitis, chronic fatigue immune dysfunction syndrome (CFIDS), chronic inflammatory demyelinating polyneuropathy, Churg-Strauss syndrome, Cicatrical pemphigoid, CREST syndrome, Crohn's disease, Discoid lupus, essential mixed cryoglobulinemia, fibromyalgia-fibromyositis, Glomerulonephritis, Guillain-Barre, Hashimoto's thyroiditis, idiopathic pulmonary fibrosis, idiopathic thrombocytopenia purpura (ITP), irritable bowel disease (IBD), IgA neuropathy, Juvenile arthritis, Lichen planus, Lupus erythematosus, Meniere's disease, mixed connective tissue disease, multiple sclerosis, Type 1 or immune-mediated diabetes mellitus, Myasthenia gravis, Pemphigus vulgaris, Pernicious anemia, Polyarteritis nodosa, Polychrondritis, Polyglandular syndromes, Polymyalgia rheumatic, Polymyositis and dermatomyositis, Primary agammaglobulinemia, Primary biliary cirrhosis, psoriasis, psoriatic arthritis, Raynauld's phenomenon, Reiter's syndrome, Rheumatoid arthritis, Sarcoidosis, Scleroderma, Sjogren's syndrome, Stiff-man syndrome, Systemic lupus erythematosus, Lupus erythematosus, Takayasu arteritis, Temporal arteristis/giant cell arteritis, ulcerative colitis, Uveitis, Vasculitides such as dermatitis herpetiformis vasculitis, Vitiligo, Wegener's granulomatosis, T cell mediated autoimmune disease, rheumatic disease, rheumatic arthritis, and lupus erythematosus.

Certain embodiments concern treating a liver condition with a composition disclosed herein. Liver conditions disclosed herein include, but are not limited to liver disease, cirrohosis, viral infections (e.g., hepatitis) and any other liver condition caused by excess inflammation or an immune disorder.

In certain embodiments disclosed herein, compositions can be used to treat an autoimmune disease in a subject. Autoimmune diseases contemplated herein include, but are not limited to, Acute disseminated encephalomyelitis (ADEM), Addison's disease, Agammaglobulinemia, alopecia greata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease (one of two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, *Erythroblastosis fetalis*, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Giant cell arteritis, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis, Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (Autoimmune thrombocytopenic purpura), IgA nephropathy, Inclusion body myositis, Chronic inflammatory demyelinating polyneuropathy, Kawasaki's disease, Lambert-Eaton myasthenic syndrome, Leukocyto elastic vasculitis, Lichen planus, Lichen sclerosus, Linear IgA disease (LAD), Lou Gehrig's disease, Amyotrophic lateral sclerosis, Lupoid hepatitis aka Autoimmune hepatitis, Lupus erythematosus, Majeed syndrome, Microscopic polyangiitis, Miller-Fisher syndrome, Guillain-Barre Syndrome, Mixed connective tissue disease, Morphea, Mucha-Habermann disease, Pityriasis lichenoides et varioliformis acuta, Multiple sclerosis, Myasthenia gravis, Myositis, Narcolepsy, Neuromyelitis optica, Devic's disease, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with

*streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome, Schnitzler syndrome, Scleritis, Scleroderma, Serum Sickness, Sjogren's syndrome, Spondyloarthropathy, Still's disease, Juvenile Rheumatoid Arthritis, Stiff person syndrome, Subacute bacterial endocarditis (SBE), Susac's syndrome, Sweet's syndrome, Sydenham chorea, Sympathetic ophthalmia, Systemic lupus erythematosis, Takayasu's arteritis, Temporal arteritis, Thrombocytopenia, Tolosa-Hunt syndrome, Transverse myelitis, Ulcerative colitis, Undifferentiated spondyloarthropathy, Undifferentiated connective tissue disease, Urticarial vasculitis, Urticarial vasculitis, Vasculitis Vitiligo and Wegener's granulomatosis.

In other embodiments, compositions disclosed herein can include treating conditions such as inflammatory conditions including, but not limited to, allergic disorders for example, arthritis, inflammatory osteolysis, asthma, chronic inflammation (e.g., from chronic viral or bacteria infections), chronic obstructive pulmonary disease (COPD), Encephalitis, inflammatory bowel disease (IBD), psoriasis (e.g., plaque psoriasis, pustular psoriasis, erythrodermic psoriasis, guttate psoriasis or inverse psoriasis), pulmonary fibrosis, undifferentiated arthropathy, undifferentitated spondyloarthropathy. Other conditions can include, but are not limited to respiratory conditions, for example, asthma, COPD, emphysema. Other lung conditions are contemplated, such as Cystic Fibrosis and bronchiolitis obliterans.

Radiation Protection and Cancer

In certain embodiments, compositions (e.g., construct compositions) and methods concern modulating adverse effects of radiation on a subject. In some embodiments, compositions and methods concern treating a subject having radiation therapy or radiation for example, when administered to a subject having cancer or suspected of developing a malignancy or for uncontrolled cellular growth. Other embodiments disclosed herein concern treating a subject having been exposed to radiation, for example, by accident or by a purposeful act in order to reduce adverse side effects of radiation treatment.

Some embodiments disclosed herein concern treatment of a subject undergoing cancer therapies. In accordance with these embodiments, a subject undergoing cancer therapies can be treated with a composition disclosed herein to reduce or prevent detrimental affects of the treatment (e.g., from radiation and/or chemotherapy treatments). Cancer treatments include, but are not limited to, treatment for bladder cancer, breast cancer, kidney cancer, leukemia, lung cancer, myeloma, liposarcoma, lymphoma, tongue cancer, prostate cancer, stomach cancer, colon cancer, uterine cancer, melanoma, pancreatic cancer, brain cancer, eye cancer, skin cancer and other known cancers.

In other embodiments, compositions disclosed herein can be used to treat a subject having cancer. Cancers contemplated for these embodiments can include, but are not limited to, fibrosarcoma, myxosarcoma, liposarcoma, chondrosarcoma, osteogenic sarcoma, chordoma, angiosarcoma, endotheliosarcoma, lymphangiosarcoma, Kaposi's sarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, melanoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, leukemia, or other known cancer.

Other embodiments include regarding radioprotection and compositions disclosed herein can concern treatment for trigeminal neuralgia, treatment for severe thyroid eye disease, treatment for pterygium, treatment for pigmented villonodular synovitis, prevention of keloid scar growth, prevention of heterotopic ossification, cosmetic, plastic or reconstructive surgical application surgery (e.g., reducing scar formation), during chemotherapy, in combination with hormone therapy, and/or as an immunotherapy combination. In certain embodiments herein, compositions containing fusion polypeptides can be used to reduce inflammation in a subject undergoing or having undergone plastic surgery. Administration of such a composition may be used to reduce inflammation and scarring of the subject.

Certain side effects can occur during radiation exposure and even as a side effect of radiation therapy or chemotherapy. Some embodiments herein concern reduction or prevention of these side effects in a subject by treating the subject with compositions disclosed herein. Compositions can include recombinant forms of AAT and/or recombinant forms of AAT carboxyterminal peptides (e.g., 80 mer, 36 mer etc.). Side effects of radiation therapy can include, but are not limited to, cellular damage, pain, swelling, local irritation, fibrosis, scaring, loss of tissue integrity, increased tissue friability, difficulty in swallowing and other symptoms associated with radiation treatment or exposure. Other side affects that can be reduced or prevented concern side effects from total body irradiation (TBI), for example during bone marrow transplantation. These side effects can include the above and in addition, acute and chronic immunodeficiency and opportunistic infections.

Some embodiments disclosed herein concern treating a subject having or suspected of developing prostate cancer. In accordance with these embodiments, a male subject having or suspected of developing prostate cancer can be treated with compositions disclosed herein before, during or after radiation and/or chemotherapy treatment(s) in order to reduce side effects attributed to these therapies. For example, side effects can be, but are not limited to, development of impotence or erectile dysfunction.

Other conditions contemplated herein include systemic lupus erythematosis (SLE, or lupus), rheumatoid arthritis, sepsis, systemic lupus erythematosis (SLE, or lupus), rheumatoid arthritis, inflammatory bowel disease, sepsis, autoimmune diseases, atherosclerosis, Alzheimer's disease, arthritis, muscular dystrophy, Downs syndrome, multiple sclerosis, stroke, neurodegenerative disorders, other inflammatory diseases or conditions and sero-negative spondyloarthropathies.

Graft Rejection and Graft Survival

In other embodiments, recombinant or fusion polypeptides (e.g., Fc-AAT or Fc-AAT fragment) contemplated herein can be used to treat a subject undergoing a transplant, such as an organ or non-organ (e.g., cellular) transplant. In certain embodiments, cellular transplantation can include bone marrow, islet cell (e.g., islet allograft), corneal cell, stem cell, skin (e.g., cellular or larger), temporary cadaver transplants of skin (e.g., soft tissue, facial or other) or conditions related to cellular transplant rejection such as graft versus host disease (GVHD). Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing bone marrow transplantation. In other embodiments, methods disclosed herein may be used to treat a subject undergoing stem cell or other cellular transplantation. In accordance with these embodiments, a subject may be treated to reduce transplantation rejection, preserve the cells of a transplant and/or prolong transplanted cell (graft) survival. Other embodiments can include treating a subject undergoing an organ transplant such as a heart, lung, intestinal, liver, pancreas, kidney or other organ transplant.

In one example, methods disclosed herein may be used to treat a subject undergoing bone marrow transplantation. In accordance with these embodiments, a subject can be treated before, during or after bone marrow transplantation to reduce or prevent graft rejection and/or GVHD in the subject.

In other embodiments, compositions and methods disclosed herein concern prevention or reducing the occurrence of organ transplant rejection. In other embodiments, compositions and methods disclosed herein concern prolonging organ transplantation. Transplants contemplated herein can concern transplantation of kidney, heart, liver, soft tissue, facial component transplant, intestinal transplants, and pancreas transplant. In addition, compositions disclosed herein can concern reduction or prevention of symptoms associated with transplantation of an organ or non-organ. Symptoms that can be reduced or prevented by treating a subject undergoing a transplant with compositions disclosed herein can include, graft rejection, kidney failure, lung failure, heart failure, mucosal ulcerations, reduced islet function (increased glucose, diabetes mellitus), graft versus host disease (GVHD), gastrointestinal (GI), ulceration, pulmonary failure, skin ulceration, coagulopathy, CNS dysfunction, and coma.

Embodiments of the present invention provide methods for promoting prolonged graft survival and function in a subject including administering to a subject in need thereof a therapeutically effective amount of a composition including a substance of recombinant AAT or fusion protein thereof and a pharmaceutically acceptable excipient.

In certain embodiments, the subject is a mammal. In some embodiments, the mammal is a human. In yet other embodiments, the subject is a male, a female, a pregnant female, an infant or a juvenile.

Yet other aspects of the present invention concern organ or cell preservation prior to transplantation. For example, cryoprotection or protection during transport or other preservation method may be enhanced by exposing an organ, tissues or cells to compositions disclosed herein. Certain embodiments herein concern using a composition disclosed herein for preserving an organ, tissue or cells in preparation for transplantation or for cryoprotection. In accordance with these embodiments, organs, tissue or cells can include any of those disclosed herein, for example, pancreatic islet cells, stem cells, bone marrow cells, kidney, liver, lung and other organ or cellular transplants.

In certain embodiments of the present invention, compositions disclosed herein can further include combination therapy. For example, combination therapies can include one or more of interferon, interferon derivatives including beta-seron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

In certain embodiments, a subject having or suspected of having a myocardial infarction can be administered a composition disclosed herein to ameliorate the symptoms or side effects of the cardiac condition. In certain embodiments, compositions disclosed herein can be used to reduce or prevent cardiac ventricular remodeling. Methods for treating any condition disclosed herein can include administering a composition before, during or after a cardiac event. In certain embodiments, compositions can be administered to a subject for a period determined by health professional to have optimum benefit after a cardiac event has occurred in a subject. For example, a subject may be treated with a composition for up to one week, up to two weeks or more following an event. In certain embodiments, compositions administered to a subject described herein can be 5-fold, 10-fold, 100-fold or 1,000 fold less than using a commercially available AAT formulation (e.g., Aralast™, Prolastin C™), such as 0.001 mg/kg to 10 mg/kg recombinant or AAT fusion molecule per dose.

Diabetes

In addition, compositions disclosed herein may be administered to any subject having diabetes to treat the disease in the subject. A subject having Type 1 or Type 2 diabetes can be administered a composition disclosed herein to treat the disease or treat the disease symptoms. These treatments can be combined with any treatment known in the art for diabetes. In certain embodiments, compositions disclosed herein can be administered to a subject at reduced levels (e.g., concentrations) compared to currently available commercial formulations to treat a subject having diabetes. In accordance with these embodiments, a subject having diabetes can be a subject having early onset diabetes Type 1 such as one diagnosed within 5 years having with for example, detectible c-peptide levels, and/or with detectible insulin production, and/or with residual islet cell function.

Other embodiments can concern using a composition disclosed herein to protect islet cells in vivo (e.g., to preserve or rejuvenate islet cell function) or in vitro (e.g., during transport for transplantation). It is contemplated that compositions disclosed herein can be used to treat a subject having diabetes that has some remaining islet cell function and/or treat islet cells prior to transplant in a subject to preserve islet cells. Therefore, a subject may be treated before, during or after islet cell transplantation. In other embodiments, diabetes treatments can include treating a subject having insulin resistant diabetes, Type I and Type II.

Cardiac Conditions

Some embodiments of the present invention comprise treating a subject having a cardiac condition or undergoing cardiac intervention (e.g., surgery, preventative treatment). In accordance with these embodiments, a subject having a cardiac condition may have one or more of the following conditions including, but not limited to, myocardial infarction, myocardial ischemia, chronic systemic arterial and venous hypertension, pulmonary arterial and venous hypertension, congenital heart disease (with and without intracardiac shunting), valvular heart disease, idiopathic dilated cardiomyopathy, infectious and non-infectious myocarditis, stress cardiomyopathy (as seen associated with critical care illnesses, physical and emotional stress, and intracranial hemorrhage and stroke), septic cardiomyopathy, atrial and ventricular arrhythmias, endocarditis, pericarditis, damage to heart muscle, cardioplegia, cardiac arrest, acute myocardial infarction (AMI), myocardial ischemia-reperfusion injury, ventricular remodeling, concentric hypertrophy, eccentric hypertrophy and any other known cardiac condition.

In certain embodiments, a subject having or suspected of having a myocardial infarction can be administered a composition disclosed herein to ameliorate the symptoms or side effects of the cardiac condition. In certain embodiments, compositions disclosed herein can be used to reduce or prevent cardiac ventricular remodeling. Methods for treating any condition disclosed herein can include administering a composition before, during or after a cardiac event. In certain embodiments, compositions can be administered to a subject for a period determined by health professional to have optimum benefit after a cardiac event has occurred in a subject. For example, a subject may be treated with a composition for up to one week, up to two weeks or more following an event. In certain embodiments, compositions administered to a subject described herein can be 5-fold, 10-fold, 100-fold or 1,000 fold less than using a commercially available AAT formulation (e.g., Aralast™, Prolastin C™), such as 0.001 mg/kg to 10 mg/kg recombinant or AAT fusion molecule per dose.

Gastrointestinal Disorders

Some embodiments of the present invention include treating a subject having a gastrointestinal order or condition (e.g., intermittent, solitary or chronic condition). In accordance with these embodiments, a subject having a gastrointestinal condition may have one or more of the following conditions including, but not limited to, inflammatory bowel disease (e.g., IBS or IBD), ulcerative colitis (UC), Crohn's disease (CD), systemic inflammatory response syndrome (SIRS), allergy-linked bowel disease, bowel disease linked to Type 1 diabetes, other colitis types (e.g., collagenous colitis, ischaemic colitis, diversion colitis, indeterminate colitis), Behcet's syndrome associated with inflammation of the bowels and other bowel disorders. In certain embodiments, symptoms or side effects of bowel disorders can be treated by compositions disclosed herein. For example, side effects of bowel disorders include, but are not limited to, skin manifestations, weight loss, colon shortening, intestinal mucosa, bowel or intestinal hyperpermeability. Certain embodiments can include treating a subject having a bowel disorder with compositions disclosed herein to reduce or prevent weight loss in a subject having the disorder.

Bacterial Conditions

Some embodiments of the present invention include treating a subject having a bacterial infection. Other embodiments can include administering a composition disclosed herein to prevent a bacterial infection in a subject. Bacterial infections contemplated herein can include, but are not limited to, Gram negative or Gram positive bacteria or mycobacterial organisms. Gram negative bacteria can include, but are not limited to, *N. gonorrhoeae*, *N. meningitidi*, *M. catarrhalis*, *H. injiuenzae*, *E. coli*, all *Klebsiela* spp., all *Enterobacter* spp., all *Serratia* spp, all *Salmonella* spp., *Proteus mirabilis*, *Proteus vulgaris*, all *Providencia* spp., all *Morganella* spp., *Pseudomonas aeruginosa*, all *Citrobacter* spp., all *Pasteurella* spp., all *Aeromonas* spp., *Pseudomonas cepacia*, all *Shigella* spp, *Stenotrophomonas maltophilia*, all *Acinetobacter* spp., all *Legionella* spp., *Y. enterocolitica*, other *Yersinoiiosis*, *H. ducreyeii*, all *Chlamyidia* spp., *Mycoplasma pneumonia*, *Mycoplasma hominis*, *Bacteroides fragilis*, *P. melaminogenica*, all *Moraxella* spp., all *Bortedella* spp., and *P. multocida*.

*Mycobacteria* contemplated herein can include, but are not limited to, *M. bovis*, *M. tuberculosis*, *Mycobacterium avium* complex (MAC) organisms, *M. intracellulare*, *M. avium*, *M. paratuberculosis*, leprosy causing (*M. leprae*, *M. flavascens*, *M. lepraemurium*, *M. microti*, *M. chelonei*, *M. africanum*, *M. marinium*, *M. buruli*, *M. fortuitum*, *M. haemophilum*, *M. kansasii*, *M. littorale*, *M. malmoense*, *M. marianum*, *M. simiae*, *M. szulgai*, *M. ulcerans*, *M. gordonae*, *M. gastri*, *M. phlei*, *M. nonchromogenicum*, *M. smegmatis*, *M. terse*, *M. trivial*, *M. scrofulaceum*, *M. xenopi*, *M. gordonae*, *M. haemophilum*, *M. genavense*, *M. simiae*, *M. vaccae*.

Gram positive bacteria contemplated herein include, but are not limited to, *C. tetani*, *C. botulinum*, *C. difficile*, Group A, B C, and G *Streptococcus*, *Streptococcus pneumonia*, *Streptococcus milleri* group, *Viridans streptococcus*, all *Listeria* spp., all *Staphylococcus* spp, *S. aureus* (MSSA), *S. aureus* (MRSA), *S. epidermidis*, *Enterococcus faecalis*, *Enterococcus faecium*, all *Clostridium* spp., *C. diptheriea*, *C. jeikium*, all *Rhodococcus* spp., all *Leukonostoc* spp. and *Bacillus anthracis* (e.g., that causes anthrax).

In certain embodiments, compositions disclosed herein can be used to treat a subject having a bacterial condition, reducing or preventing onset of a bacterial associated condition.

Viral Conditions

Some embodiments of the present invention include treating a subject having a viral infection. Other embodiments can include administering a composition disclosed herein to prevent a viral infection or treat a viral infection in a subject. Viral infections contemplated herein can include, but are not limited to, Human Immunodeficiency Virus (HIV) AIDS, influenza virus (e.g., type A, B, C, influenza A H1N1, H1N2, H3N2, H9N2, H7N2, H10N7), Herpes zoster, Herpes simplex, human papilloma virus, Variola major virus (small pox), Lassa fever virus, avian flu, AIDS Related Complex, Chickenpox (*Varicella*), Cytomegalovirus, Colorado tick fever, Dengue fever, Ebola haemorrhagic fever, Hand, foot and mouth disease, Hepatitis, HPV, infectious mononucleosis, Mumps, Poliomyelitis, Progressive multifocal leukencephalopathy, Rabies, Rubella, SARS, viral encephalitis, viral gastroenteritis, viral meningitis, West Nile disease, Yellow fever, Marburg haemorrhagic fever, Measles and other viral-related disorders.

Other embodiments disclosed herein concern reducing or preventing cancer induced by a virus by inhibiting viral replication and/or infection in a subject. Cancers induced by viruses can include, but are not limited to, Rous sarcoma induced cancer, human papilloma virus (HPV) induced cancer, polyoma induced cancer, Hepatitis B virus induced cancer, fibrosarcoma, myxosarcoma, liposarcoma, chondrosarcoma, osteogenic sarcoma, angiosarcoma, chordoma, endotheliosarcoma, lymphangiosarcoma, lymphangioendotheliosarcoma, mesothelioma, synovioma, Ewing's tumor, leiomyosarcoma, rhabdomyosarcoma, rhabdosarcoma, colorectal carcinoma, pancreatic cancer, breast cancer, melanoma, prostate cancer, ovarian cancer, squamous cell carcinoma, basal cell carcinoma, sebaceous gland carcinoma, adenocarcinoma, sweat gland carcinoma, papillary carcinoma, hepatoma, cystadenocarcinoma, papillary adenocarcinomas, bronchogenic carcinoma, medullary carcinoma, renal cell carcinoma, seminoma, bile duct carcinoma, cervical cancer, Wilms' tumor, embryonal carcinoma, lung carcinoma, choriocarcinoma, testicular tumor, bladder carcinoma, epithelial carcinoma, small cell lung carcinoma, craniopharyngioma, medulloblastoma, astrocytoma, glioma, ependymoma, pinealoma, hemangioblastoma, acoustic neuroma, oligodendroglioma, menangioma, neuroblastoma, retinoblastoma, myeloma, lymphoma, and leukemia. Yet other embodiments concern viral pneumonia and bronchial pneumonia.

In certain embodiments, compositions disclosed herein can be used to treat a subject having a viral infection, reducing or preventing onset of a viral associated condition. For example, compositions disclosed herein can be used to treat a subject having a viral infection to reduce transmission of the virus and reduce viral replication in the subject (e.g., influenza or other disease transmitted from subject to subject).

In another exemplary embodiment, compositions disclosed herein can be used to treat gout in a subject to reduce inflammation and production of uric acid crystals in a subject. For this, a model of gouty arthritis can be employed based on roles of IL-1β in the inflammation of gout (model previously presented using commercially available formulations). In this model, MSU and C18 fatty acids can be mixed and injected into the subpatellar space of C57 Black 6 mice as a mouse model. Recombinant human Fc-AAT can be injected intra-articularly (i.a.) at 2 µg into the subpatellar space alone of the mice and examined. Into other test group, mice can be injected with MSU/C18. In another set of mice, the combination of MSU/C18 plus compositions disclosed herein can be injected. Knees of mice can be then be examined for inflammation as done in the model with plasma-derived AAT. In one example, the number of cells infiltrating the synovium can be observed.

Constructs of Various Peptides

Embodiments herein provide for generating and using recombinant AAT or recombinants having one or more carboxyterminal peptides derived from AAT (e.g., a carboxyternminal peptide of AAT found in the last 80 amino acids of AAT or a carboxyterminal peptide of AAT found in the last 36 amino acids of AAT etc). In accordance with these embodiments, fusion polypeptides can be generated that are linked to immune molecules to for example, increase half-life of the peptide and/or use the immune molecule to further direct the fusion polypeptide through immune molecule binding etc. Constructs designed herein can be as active as commercially available formulations or more active in a particular activity, for example, anti-inflammatory activities than a commercial formulation.

In one embodiment of the present invention, a composition may include constructs for treating a subject in need of AAT therapy (e.g., mammalian derived AAT treatment or supplementation) for example, administering a series of peptides including carboxyterminal amino acid peptides corresponding to AAT and derivatives thereof. These peptides can include, pentapetides including, FVFLM (SEQ ID NO:2), FVFAM (SEQ ID NO:3), FVALM (SEQ ID NO:4), FVFLA (SEQ ID NO:5), FLVFI (SEQ ID NO:6), FLMII (SEQ ID NO:7), FLFVL (SEQ ID NO:8), FLFVV (SEQ ID NO:9), FLFLI (SEQ ID NO:10), FLFFI (SEQ ID NO:11), FLMFI (SEQ ID NO:12), FMLLI (SEQ ID NO:13), FIIMI (SEQ ID NO:14), FLFCI (SEQ ID NO:15), FLFAV (SEQ ID NO:16), FVYLI (SEQ ID NO:17), FAFLM (18), AVFLM (SEQ ID NO:19), and any combination thereof that is part of a fusion construct.

In other embodiments, AAT peptides contemplated for use in constructs, pharmaceutical compositions and methods herein are also intended to include any and all of those specific AAT peptides of SEQ ID NO:1 or SEQ ID NO:33 (naturally-occurring AAT of 394 amino acids, the most common form is the M type with subtypes M1, M2, M3 etc. are also contemplated herein) associated with the carboxyterminal amino acids. All AAT polypeptides are contemplated of use in methods disclosed herein, that possess anti-inflammatory activity and/or immune regulatory activity. Any combination of consecutive amino acids simulating AAT or AAT-like activity may be used, such as amino acids ranging from 315-394, amino acids ranging from 325-384, 358-394, 340-380 etc. In addition, combinations of consecutive amino acid sequences such as 5-mers, 10-mers, 15-mers, 20-mers, 25-mers, 30-mers, 35-mers etc. of the carboxyterminus can also be used. For example, any combinations of consecutive amino acids of 5-mers, 10-mers, 15-mers, 20-mers from SEQ ID NO:1 AAs 314-394 can be used in developing or purifying a construct contemplated herein.

Certain embodiments concern generating a recombinant fusion polypeptide or protein including linking an entire AAT molecule (e.g., SEQ ID NO: 1 or 33) or a peptide molecule derived from the carboxyterminal amino acid region of AAT, to an IgG or fragment thereof. One common form of AAT is denoted by SEQ ID NO:33. One construct contemplated herein is referenced as SEQ ID NO:32 (e.g., whole AAT, a leader sequence and an Fc portion of an immunoglobulin molecule) and SEQ ID NO:48 (whole AAT and an Fc portion of an immunoglobulin molecule with a linker) These constructs can be used as a dimer or as a monomeric form in compositions disclosed herein. In accordance with these embodiments, a pharmaceutically acceptable composition can include a dimer of Fc-AAT or a monomer of Fc-AAT or AAT cleaved from the Fc or combinations thereof, and a pharmaceutically acceptable excipient. In addition, point mutations can be made in the Fc region to reduce the flexibility of the hinge region and generate novel Fc-AAT molecules.

```
SEQ ID NO: 33:
EDPQGDAAQKTDTSHHDQDHPTFNKITPNLAEFAFSLYRQLAHQSN

STNIFFSPVSIATAFAMLSLGTKADTHDEILEGLNFNLTEIPEAQI

HEGFQELLRTLNQPDSQLQLTTGNGLFLSEGLKLVDKFLEDVKKLY

HSEAFTVNFGDTEEAKKQINDYVEKGTQGKIVDLVKELDRDTVFAL

VNYIFFKGKWERPFEVKDTEEEDFHVDQATTVKVPMMKRLGMFNIQ

HCKKLSSWVLLMKYLGNATAIFFLPDEGKLQHLENELTHDIITKFL
```

```
                     -continued
ENEDRRSASLHLPKLSITGTYDLKSVLGQLGITKVFSNGADLSGVT

EEAPLKLSKAVHKAVLTIDEKGTEAAGAMFLEAIPMSIPPEVKFNK

PFVFLMIEQNTKSPLFMG KVVNPTQK
```

In other embodiments, AAT protease binding domains can be mutated in order to reduce or eliminate the protease function of the molecule and not inhibit elastase activity; these molecules can be used in any construct contemplated herein. In certain embodiments, a mutated AAT can be used to generate an AAT construct by methods disclosed herein. In other embodiments, a mutated molecule (e.g., having reduced or essentially no protease activity) retains its anti-inflammatory effects and/or immunomodulatory effects and can be used as an anti-inflammatory molecule in a subject having a need for AAT therapy. One skilled in the art would understand a non-protease binding domain of AAT as well as what is termed the carboxyterminal last 80 amino acids of naturally-occurring AAT.

In each of the above-recited methods, α1-antitrypsin or carboxyterminal peptide derivatives thereof are contemplated for use in a composition herein. These peptide derivatives may include but are not limited to amino acid peptides containing the last 80 carboxyterminal derived amino acids of AAT, GITKVFSNGA (SEQ ID NO:20), DLSGVTEEAP (SEQ ID NO:21), LKLSKAVHKA (SEQ ID NO:22), VLTIDEKGTE (SEQ ID NO:23), AAGAMFLEAI (SEQ ID NO:24), PMSIPPEVKF (SEQ ID NO:25), NKPFVFLMIE (SEQ ID NO:26), QNTKSPLFMG (SEQ ID NO:27), KVVNPTQK (SEQ ID NO:28), LEAIPMSIPPEVKFNKPFVFLM (SEQ ID NO:29); and LEAIPMSIPPEVKFNKPFVF (SEQ ID NO:30), GADLSGVTEEAPLKLSKAVHKAVLTIDEKGTEAAGAMFLEAIPMSIPPEVKFNKPFVFLMIEQNTKSPLFMGKVVNPTQK (SEQ ID NO:31), SEQ ID NO:34 or any combination thereof. In certain embodiments, the carboxyterminal peptides of AAT are 80%, or 85%, or 90%, or 95%, or 99% identical to the naturally occurring M type amino acid sequence identified by SEQ ID NO. 33. In certain embodiments, about 2, about 3, or about 4, or about 5 amino acids can vary (e.g., various point mutations) from an 80-mer from the carboxy terminal of M type sequence.

Certain embodiments include compositions of the construct of SEQ ID NO: 32 or SEQ ID NO: 48. In accordance with these embodiments, the compositions can be pharmaceutical compositions.

In certain embodiments, compositions of recombinant AAT or AAT-derived carboxyterminal peptides capable of binding to SEC receptors or compositions with AAT-like activities may be administered to a subject in need thereof. As disclosed herein the carboxy terminal region of AAT includes the last 80 amino acids of SEQ ID NO:31 or SEQ ID NO:33 or other human AAT molecule or other naturally occurring AAT molecule. In other embodiments, peptides derived from AAT can include 5-mers, 10-mers, 20-mers, 25-mers, 30-mers, 35-mers, 40-mers, 50-mers, and up to an 80 mer of an AAT molecule wherein any of the contemplated peptides have no significant serine protease inhibitor activity, are derived from the carboxyterminus of AAT and are capable of being used for treating subjects undergoing radiation or subjects exposed to large doses of radiation by accident or other cause.

In one embodiment, a construct may include compounds that engage or associate with the SEC receptor. In some of the recited methods, an AAT-mutant or AAT derived peptide (e.g., mammalian derived) having no significant serine protease inhibitor activity is contemplated for use within the compositions and uses of the present invention that can include a series of peptides including carboxyterminal amino acid peptides corresponding to AAT. In addition, combinations of amino acid 5-mers or 10-mers or 20-mers or 30-mers or more can also be used. For example, one or more 5-mers or 10-mers or 20-mers etc can include consecutive amino acids starting from AA 315 and ending with AA 394 of naturally occurring AAT represented as SEQ ID NO:1. As contemplated herein, the later half of a sequence toward the carboxy end is referred to as the carboxyterminus. In certain embodiments, the carboxyl domain of AAT going backwards from the carboxyl terminus is defined as those amino acids most conserved among the difference species and do not participate in the protease binding domain of AAT. In addition, in other embodiments, AAT protease binding domain can be mutated in order to reduce or eliminate the protease function of the molecule and this molecule can be used in any composition contemplated herein. In other embodiments, a mutated AAT-related molecule can retain its anti-inflammatory and/or immunomodulatory effects. Also contemplated herein is that the carboxyl domain is the non-protease binding domain that has other AAT activities. One skilled in the art would understand a non-protease binding domain of AAT.

In each of the above-recited methods, compositions herein may include peptides derived from the carboxyterminus of AAT. In certain embodiments, AAT-associated molecules used in the methods and compositions herein can include, but are not limited to, compositions of SEQ ID NO:1, naturally occurring AAT (394 AA length molecule making up approximately 90% of AAT isolated from serum), other AAT M-types or other AAT molecules.

Of use herein, commercially available formulations for comparisons and/or controls with recombinant of fusion molecules disclosed herein can include Aralast™ (Baxter), Zemaira™ (Aventis Behring), Prolastin™ or ProlastinC™ (Talecris), Aprotonin™ or Trasylol™ (Bayer Pharmaceutical Corporation), Ulinistatin™ (Ono Pharmaceuticals, Inc.), and inhalation and/or injectable AAT (Kamada, Ltd., Israel), or any other commercially available AAT compositions or any combination thereof.

Other embodiments concern mutants of human AAT where the mutant has increased anti-inflammatory activity. Any method known in the art for generating mutants is contemplated. Some embodiments include using site-directed mutageneis to generate a hATT having no significant serine protease inhibitor activity (see Examples section and pEF-hAAT). In some embodiments, compositions can be a pharmaceutical composition having a mutated human alpha-1 antitrypsin (hAAT) wherein the AAT includes AAT with one or more point mutations at AAT's protease-binding site within AAT's reactive center loop (RCL). These one or more point mutations can significantly reduces or eliminate serine protease inhibition activity of the AAT compared to a control human AAT. Other methods include disrupting the serine protease inhibiting region of hAAT by other disruption methods such as heating hAAT, or generating another mutant such as an RCL mutant with a modified proline to cysteine residue at position 357 within the RCL to eliminate or dramatically reduce serine protease inhibitor activity. In certain embodiments, a fusion molecule can include linking FC (e.g., IgG1, 2, 3 or 4) to an AAT mutant having one or more point mutations at one or more amino acids within the RCL, (e.g., amino acids 355-363 of native AAT), wherein the AAT mutant has no significant serine protease inhibition activity and the RCL remains intact.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g., pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

Pharmaceutical compositions containing AAT or peptide fragment thereof, or analog thereof, or mutant thereof, or a functional derivative thereof (e.g., pharmaceutical chemical, protein, peptide of some of the embodiments) may be administered to a subject, for example by subcutaneous, intravenous, intracardiac, intracoronary, intramuscular, by oral administration, by inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the composition may be administered intranasally, such as inhalation.

Some embodiments disclosed herein concern using a stent or a catheter to deliver one or more chemotherapeutic agents (e.g., along with compositions disclosed herein) to a subject having or suspected being treated for cancer. Any stent or other delivery method known in the art that can deliver one or more agents directly to tumor site is contemplated. These delivery techniques can be used alone or in combination with other delivery methods.

A compound (e.g., a peptide, protein, fusion protein or mixture thereof) may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used.

Sterile injectable solutions can be prepared by incorporating active compound (e.g., a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art. Solutions of the active compounds as free-base or pharmacologically acceptable salts can be prepared in water suitably mixed with a surfactant, such as hydroxypropylcellulose.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition such as daily, bi-weekly, weekly, bi-monthly etc. Pharmaceutical compositions are administered in an amount, and with a frequency, that is effective to modulate side effects. The precise dosage and duration of treatment may be determined empirically using known testing protocols or by testing the compositions in model systems known in the art and extrapolating therefrom. Dosages may also vary with the severity of the condition. In certain embodiments, the composition range can be between 10 and 75 mg/kg introduced daily or weekly to a subject. A therapeutically effective amount of $\alpha$1-antitrypsin, peptides, or drugs that have similar activities as $\alpha$1-antitrypsin or peptides can be also measured in molar concentrations and can range between about 1 nM to about 2 mM.

In another embodiment, nasal solutions or sprays, aerosols or inhalants may be used to deliver the compound of interest. Additional formulations that are suitable for other modes of administration may include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Liposomes or microparticles can be used as a therapeutic delivery system and can be prepared in accordance with known laboratory techniques. In addition, dried lipids or lyophilized liposomes prepared as previously described may be reconstituted in a solution of active agent (e.g., nucleic acid, peptide, protein or chemical agent), and the solution diluted to an appropriate concentration with a suitable solvent known to those skilled in the art. The amount of active agent encapsulated can be determined in accordance with standard methods.

In some embodiments, pharmaceutical construct compositions concerns a construct derived from an AAT molecule having no significant serine protease inhibitor activity but having other $\alpha$1-antitrypsin activity or analog thereof may be used in a single therapeutic dose, acute manner or a chronic manner to treat a subject. For example, the fusion polypeptides contemplated herein can be a fusion polypeptide having no significant protease inhibition activity.

In certain embodiments, compositions herein can be administered orally, systemically, via an implant, time released or slow-release compositions (e.g., gel, microparticles etc.), intravenously, topically, intrathecally, subcutaneously, by inhalation, nasally, or by other means known in the art or a combination thereof.

Expression Proteins and Constructs

Once the target gene or portion of a gene has been determined, the gene can be inserted into an appropriate expression system. The gene can be expressed in any number of different recombinant DNA expression systems to generate large amounts of the polypeptide product, which can then be purified and used in compositions and methods disclosed herein.

Examples of expression systems known to the skilled practitioner in the art include bacteria such as *E. coli*, yeast such as *Pichia pastoris*, baculovirus, and mammalian expression systems such as in Cos or CHO cells. A complete gene can be expressed or, alternatively, fragments of the gene encoding portions of polypeptide can be produced.

The AAT gene or gene fragment encoding a fusion polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Amino acid sequence variants of the polypeptide may also be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of site-directed mutagenesis such as those described herein for removing the transmembrane sequence.

Amino acid sequence variants of the polypeptide may be substitutional, insertional or deletion variants. Deletion variants lack one or more residues of the native protein which are not essential for function or immunogenic activity, and are exemplified by the variants lacking a transmembrane sequence.

The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with some embodiments herein one could prepare an expression vector that comprises one of the claimed isolated nucleic acids under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F—, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (tip) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographa californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized to produce molecules contemplated herein, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In certain cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable but not invasive and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators.

In certain embodiments, eukaryotic host cells can express desired polypeptides, and are often used for that purpose. They can be obtained by introduction of a DNA molecule disclosed herein, preferably in the form of an expression cassette, into the cells. In certain embodiments, the expression cassette is integrated in the genome of the host cells of interest, which can be in different positions in various host cells, and selection will provide for a clone where the transgene is integrated in a suitable position, leading to a host cell clone with desired properties in terms of expression levels, stability, and growth characteristics etc. Selection for cells containing the DNA of the target molecules can be performed by selecting for the selectable marker polypeptide, using routine methods known by one skilled in the art.

Host cells are from a stable clone that can be selected and propagated according to standard procedures known to one skilled in the art. A culture of such a clone is capable of producing polypeptides of interest.

Introduction of nucleic acid that is to be expressed in a cell, can be done by one of several methods, which as such are known to one skilled in the art, also dependent on the format of the nucleic acid to be introduced. Methods can include but are not limited to transfection, infection, injection, transformation, and the like. Suitable host cells that express the polypeptide of interest can be obtained by any selection process known in the art.

In certain embodiments, a DNA molecule of interest is integrated into the genome of the eukaryotic host cell. Selection for the presence of the selectable marker polypeptide, and hence for expression, can be performed during the initial obtaining of the cells. In certain embodiments, a selection agent is present in the culture medium at least part of the time during the culturing, either in sufficient concentrations to select for cells expressing the selectable marker polypeptide or in lower concentrations. In certain embodiments, a selection agent is no longer present in the culture medium during the production phase when the polypeptide is expressed. A polypeptide of interest can be any peptide or protein, and may be a monomeric protein or a (part of a) multimeric protein (e.g., dimer). A multimeric protein comprises at least two polypeptide chains.

In certain aspects, provided are methods for generating a host cell expressing a polypeptide of interest, the method comprising introducing into a plurality of precursor cells a DNA molecule or an expression cassette of the invention, culturing the generated cells under selection conditions and selecting at least one host cell producing the polypeptide of interest.

Also provided are methods for producing one or more polypeptides of interest, the method comprising culturing host cells of the invention. Culturing a cell is done to enable it to metabolize, and/or grow and/or divide and/or produce recombinant proteins of interest. This can be accomplished by methods well known in the art, and includes but is not limited to providing nutrients for the cell. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

Conditions for growing or multiplying cells (see, e.g., Tissue Culture, Academic Press, Kruse and Paterson, editors (1973)) and the conditions for expression of the recombinant product are known to one skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In certain embodiments, the expressed protein is collected (isolated), either from the cells or from the culture medium or from both. It may then be further purified using known methods, e.g., filtration, column chromatography, etc., by methods generally known in the art.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression can be used. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase, hypoxanthine-guanine phosphoribosyltransferase, and adenine phosphoribosyltransferase genes, in tk-, hgprt- or aprt-cells, respectively. Also, antimetabolite resistance may be used as the basis of selection for dhfr, that confers resistance to methotrexate; gpt, that confers resistance to mycophenolic acid; neo, that confers resistance to the aminoglycoside G-418 and hygro, that confers resistance to hygromycin or any other method known the art.

It is contemplated that the isolated nucleic acids of the invention may be "overexpressed", e.g., expressed in increased levels relative to its natural expression in human prostate, bladder or breast cells, or even relative to the expression of other proteins in the recombinant host cell. Such overexpression may be assessed by a variety of methods, including, but not limited to, radio-labeling and/or protein purification. However, simple and direct methods are preferred, for example, those involving one-step purification processes (e.g., Protein A affinity), SDS-PAGE and protein staining or Western blotting, followed by quantitative analyses, such as densitometric scanning of the resultant gel or blot. An increase in the level of recombinant or fusion protein or peptide in comparison to the level in controls is indicative of overexpression, as is a relative abundance of a target protein in relation to other proteins produced by the host cell and, e.g., visible on a gel or readily isolatable by methods contemplated herein.

It is contemplated that a construct generated herein using an immune molecule (e.g., Fc portion) can be isolated using various affinity columns or affinity matrices (e.g., Protein A). In certain embodiments, purification of constructs disclosed herein can include using a Protein A column or Protein A matrix or the like (e.g., Pierce, Bio-Rad or other IgG purification/isolation kits). In certain embodiments, purification of constructs disclosed herein can be performed using minimal steps to preserve anti-inflammatory or immune modulatory activity or other AAT-related activities from degradation etc. In accordance with these embodiments, purification of constructs contemplated herein may be by a single step (e.g., protein A column purification of Fc-AAT molecules) (See for example Kin-Ming et al. Protein Engineering vol. 11 no. 6 pp. 495-500, 1998; expression/Fc/Fc-X/fusion protein; and diabody technologies).

It is contemplated herein that a nucleic acid encoding any protein or peptide capable of reversibly binding to itself (e.g., through disulfide or other binding) can be used to generate AAT constructs disclosed herein. These constructs can be used as doublets or dimers of AAT for increased purification with reduced loss of function. In certain embodiments, these constructs can be used in compositions disclosed herein as a dimeric molecule for use in therapeutic applications or for research purposes. In accordance with some of these embodiments, a fragment or portion of an immune molecule linked to AAT or the carboxyterminal fragment can be inert or essentially non-immunogenic unless increased immugenicity is desired for treatment purposes. It is contemplated that constructs described herein can be used to induce beneficial immune or inflammatory effects; or reduce or eliminate adverse immune or inflammatory effects by for example, reducing the presence of certain pro-inflammatory cytokines.

Isolated Proteins

Certain embodiments pertain to isolated proteins, and biologically active peptides thereof. In one embodiment, native polypeptide can be isolated from cells or tissue sources by an appropriate purification scheme using standard protein purification techniques. In certain embodiments, the native polypeptide may be mutated or otherwise treated to reduce or eliminate serine protease inhibitor activity and then isolated for use in constructs described herein. In certain particular embodiments, serine protease inhibitor activity is reduced where no significant activity remains. In another embodiment, polypeptides contemplated herein are produced principally by recombinant DNA techniques. Alternative to recombinant expression, a polypeptide can be synthesized chemically using standard peptide synthesis techniques. Any of the peptide or protein molecules contemplated of use in compositions disclosed herein can be compositions having serine protease inhibitor activity or having no significant serine protease inhibitor activity depending on need of a subject or use to treat or prevent a condition. For example, AAT compositions may be treated in order to reduce or eliminate serine protease inhibitor activity or an AAT polypeptide may be isolated wherein the polypeptide has reduced or no significant serine protease inhibitor activity. These AAT molecules can then be used in constructs disclosed herein for rapid production and purification.

An "isolated" or "purified" protein or biologically active portion thereof is substantially free of cellular material or other contaminating proteins from the cell (e.g., from a clone) or tissue source from which the protein is derived, or substantially free of chemical precursors or other chemicals when chemically synthesized. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

In certain embodiments, nucleotides that encode polypeptides can be inserted to any construct known in the art for generating a peptide or protein. These peptides can include a polypeptide having a consecutive amino acid sequence corresponding to a portion or all of the last 80 amino acids of carboxyterminus of AAT or AAT allele. Other useful proteins are substantially identical to any portion of the carboxyterminus, and retain the functional activity of the peptide of the corresponding naturally-occurring protein yet differ in amino acid sequence due to natural allelic variation or mutagenesis. These polypeptides can be used in any construct contemplated herein (e.g., immune molecule linked constructs (Fc))

Some compositions disclosed herein may be used as therapeutic agents in the treatment of a physiological condition caused in whole or part, by excessive serine protease activity. In addition, a physiological condition can be inhibited in whole or part. Peptides contemplated herein may be administered in a composition as free peptides constructs or pharmaceutically acceptable salts thereof. Peptides may be administered to a subject as a pharmaceutical composition, which, in most cases, can include the peptide construct and/or pharmaceutical salts thereof with a pharmaceutically acceptable carrier.

Biologically active portions of a polypeptide of the invention include polypeptides including amino acid sequences sufficiently identical to or derived from the amino acid sequence of the protein (e.g., the amino acid sequence shown in any of SEQ ID NOs:2 to 31, 34 which exhibit at least one activity of the corresponding full-length protein, other than serine protease inhibition activity). A biologically active portion of a protein of the invention can be a polypeptide, which is, for example, 5, 10, 20, 30, 40 or more amino acids in length. Moreover, other biologically active portions in which other regions of the protein are deleted, can be prepared by recombinant techniques and evaluated for one or more of the functional activities of the native form of a polypeptide disclosed herein. Any of these polypeptides can be linked to an immune molecule wherein the peptide retains anti-immune and or anti-inflammatory activities or serine protease inhibition activities.

Variants of AAT molecules having no significant serine protease activity can be generated by mutagenesis, e.g., discrete point mutation or truncation. For example, a point mutation may be generated in AAT or peptide derivative thereof that still leaves the reactive center loop intact (RCL) while interfering with or preventing serine protease binding capabilities with the AAT or peptide but retaining its ability to modulate radiation adverse effects. An agonist can retain substantially the same, or a subset, of the biological activities of the naturally occurring form of the protein except no significant serine protease activity remains. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Fusion Polypeptides

In certain embodiments, agents such as AAT and/or analog thereof, or peptide derivative or fragment thereof may be part of a fusion polypeptide (AAT-related molecules). In certain examples, a fusion polypeptide may include AAT (e.g., naturally occurring mammalian al-antitrypsin) or peptide fragment thereof and a different amino acid sequence or peptide linked to or associated with the AAT-related molecules that can be an immunofragment such as an IgG fragment (e.g., Fc or mutant thereof). In addition, a fusion polypeptide disclosed herein can include a pharmaceutically acceptable carrier, excipient or diluents for delivery to a subject in need thereof. Any known methods for generating a fusion protein or fusion peptide are contemplated herein.

In yet another embodiment, AAT polypeptide or peptide fusion protein can be a GST fusion protein in which is fused to the C-terminus of GST sequences. Fusion expression vectors and purification and detection means are known in the art. Expression vectors can routinely be designed for expression of a fusion polypeptide of the invention in prokaryotic (e.g., *E. coli*) or eukaryotic cells (e.g., insect cells (using baculovirus expression vectors), yeast cells or mammalian cells) by means known in the art. In yet another embodiment, a nucleic acid of the invention can be expressed in mammalian cells using a mammalian expression vector as described in the art. In other embodiments, AAT polypeptide can be a his-tagged fusion molecule.

Clones

Other embodiments disclosed herein can include creating and isolated clones of fusion or recombinant molecules disclosed herein. In certain embodiments, a clone contemplated herein can be from an Fc-AAT molecule (e.g., full length AAT or peptide fragment thereof) with linker region having increased activity compared to control AAT (e.g., commercially available or native isolated AAT). In other embodiments, other clones concern an IgG2 molecule linked to AAT or fragment derivative thereof.

Combination Therapies

Any of the embodiments detailed herein may further include one or more a therapeutically effective amount of cancer-related medications. These therapies can include, but are not limited to, aspirin and other antiplatelet therapy including for example, clopidogrel, prasugrel, ticagrelor, abciximab, eptifibatide, tirofiban; heparin and derivatives; direct thrombin inhibitors or Xa inhibitors; warfarin; angiotensin converting enzyme inhibitors or angiotensin receptor blockers; beta- and alpha-adrenergic receptor blockers; calcium channel blockers; HMGCoA reductase inhibitors (e.g., statins); niacin and derivatives; fenofibrate; fish oil; aldosterone blockers; hydralazine and nitroderivates; phosphodiesterase inhibitors; direct guanylil cyclase activators, anti-microbial drugs, anti-inflammatory agent, immunomodulatory agent, or immunosuppressive agent or combination thereof.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents contemplated of use herein can include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole, (sulfamethoxazole/trimethoprim), and pentamidine isethionate.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents that treat the immune, vascular, or lymphatic systems or any combination thereof.

Anti-inflammatory or immunomodulatory drugs or agents contemplated of use herein can include, but are not limited to, interferon derivatives, e.g., betaseron, β-interferon; prostane derivatives, iloprost, cicaprost; glucocorticoids such as cortisol, prednisolone, methylprednisolone, dexamethasone; immunsuppressive agents such as cyclosporine A, FK-506, methoxsalen, thalidomide, sulfasalazine, azathioprine, methotrexate; lipoxygenase inhibitors, e.g., zileutone, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukines, other cytokines, T-cell-proteins; antibodies against receptors of interleukins, other cytokines, and T-cell-proteins.

Other agents of use in combination with compositions herein can be molecules having serine protease inhibitor activity. For example other serine protease inhibitors contemplated of use herein can include, but are not limited to, leukocyte elastase, thrombin, cathepsin G, chymotrypsin, plasminogen activators, and plasmin.

In addition, other combination compositions of methods disclosed herein can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. In certain embodiments, antibody-based therapies may be used as induction therapy in combination with the compositions and methods disclosed herein.

Subjects contemplated herein can include human subjects, male or female, adult or child, infant, or fetus, or other subjects such as non-human subjects, including but not limited to, primates, dogs, cats, horses, cows, pigs, guinea pigs, birds and rodents.

AAT

Human AAT is a single polypeptide chain with no internal disulfide bonds and only a single cysteine residue normally intermolecularly disulfide-linked to either cysteine or glutathione. One reactive site of AAT contains a methionine residue, which is labile to oxidation upon exposure to tobacco smoke or other oxidizing pollutants. Such oxidation reduces the elastase-inhibiting activity of AAT; therefore substitution of another amino acid at that position, e.g., alanine, valine, glycine, phenylalanine, arginine or lysine, produces a form of AAT which is more stable. Native AAT can be represented by the formula of SEQ ID NO:1 or 33 or other known naturally-occurring AAT molecules found in mammalian subjects.

Any means known for producing molecules (e.g., fusion or recombinant molecules) disclosed herein is contemplated (e.g., in mammalian cells, by bacteria, by fungi, by algae or other organisms or produced in plants).

Kits

In still further embodiments, kits for convenient use with compositions, constructs (e.g., recombinant and/or fusion molecules) and methods described above are contemplated. Kits may include AAT fusion or recombinant constructs (e.g., Fc-AAT; Fc-mutant AAT, Fc-AAT peptide fragment, IgG2 mutant linked to AAT or carboxyterminal derivative of AAT), constructs of one or more peptides derived from AAT, a mutant AAT construct composition, a mutant AAT molecule associated with a gene therapy delivery system or other combinations. Small molecules, proteins or peptides may be employed for use in any of the disclosed compositions. In addition, other agents such as anti-bacterial agents, immunosuppressive agents, anti-inflammatory agents may be provided in the kit. Kits can include, suitable container means (e.g., vessel, vial, tube etc), a protein or a peptide or analog agent, and optionally one or more additional agents.

The kits may further include a suitably aliquoted construct composition of the encoded protein or polypeptide antigen, a clone for expressing a construct disclosed herein, whether labeled or unlabeled, as may be used to prepare a construct described herein of use in compositions disclosed herein and for therapeutic applications described.

Containers of the kits will generally include at least one vial, test tube, flask, bottle, syringe or other container means or other delivery device (e.g., a stent or catheter). A kit will also generally contain a second, third or other additional container into which other combination agents may be placed. Such containers may include injection or blow-molded plastic containers into which the desired vials are retained.

In certain embodiments, a kit can include a composition including, but not limited to, constructs of AAT, AAT fragment, or an AAT analog or polypeptide, having no significant serine protease inhibitor activity. In accordance with these embodiments, a kit can contain AAT or an analog thereof having no significant serine protease inhibitor activity.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the some embodiments which are disclosed and still obtain a like or similar result without departing from the spirit and scope of the invention.

Generation of Expression Plasmid for Production of Recombinant Human AAT

Example 1

In one exemplary method, Fc-AAT constructs can be generated as indicated in FIG. 1. For example, human AAT sequences can be inserted into an expression vector, pCA-GGS. In this exemplary method, human AAT cDNA of 1260 base pairs was isolated from a human liver library and inserted into pCAGGS as illustrated in FIG. 1. Other AAT molecules or peptide fragments thereof can be used in place of the 1260 bp sequence if desired. In this example, Chinese Hamster Ovarian (CHO) cells were transfected with the plasmid to generate a cell capable of producing the construct. Using limiting dilution, AAT clones were selected and grown in serum free media. The supernatants were collected, pooled and analyzed for AAT fusion molecules. Using an antibody to human AAT, a band of about 55 kDa was observed on Western blots (data not shown). In this example, a human IgG1 Fc receptor was used in order to purify recombinant AAT using the Protein A. Clones producing the fusion molecule were identified and aliquots were frozen for future use.

Example 2

Figure 2A:
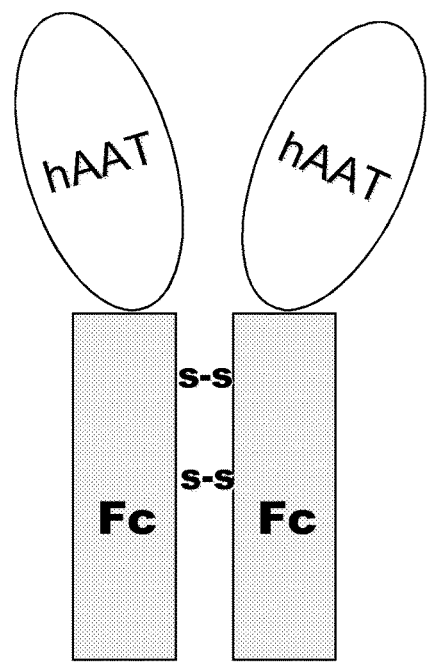
FIG. 2A represents a schematic of human AAT constructs with associated immune molecules contemplated of use for some embodiments disclosed herein.

In another exemplary method, constructs depicted in FIGS. 1 and 2A can be purified and used for methods or therapeutic treatment for any condition known related to commercially available AAT compositions or other disclosed AAT compositions. In certain embodiments, a dimer of AAT or an AAT fragment linked to an immune molecule can be used.

In certain exemplary methods, human Fc IgG plasmids (e.g., IgG1, IgG2, IgG3, IgG4, and also IgD etc) can be purchased from Qiagen (e.g., IgG1, IgG2, IgG3, IgG4, and also IgD etc). The human cDNA was excised and inserted into the human Fc vector via PCR cloning. The in-frame sequence was performed for validation. The plasmid was transfected into CHO cells and after limiting dilutions to obtain single clones, several stable clones were isolated. The stable clones were expanded and further selected using serum-free medium. Large scale cell culture was performed and the supernatants collected and pooled.

The supernatant constructs were purified using a single-step Protein A matrix. Hhuman Fc-AAT was eluted using glycine (pH 2.4) and then rapidly neutralized to pH 7.4. SDS PAGE revealed a single band under reducing conditions. In one exemplary method, the purified Fc-AAT was compared with commercially available Aralast™ for inhibition of elastase activity. Clones having an Fc-AAt construct were identified, expanded and aliquots were frozen and stored for later use.

Figure 2B:
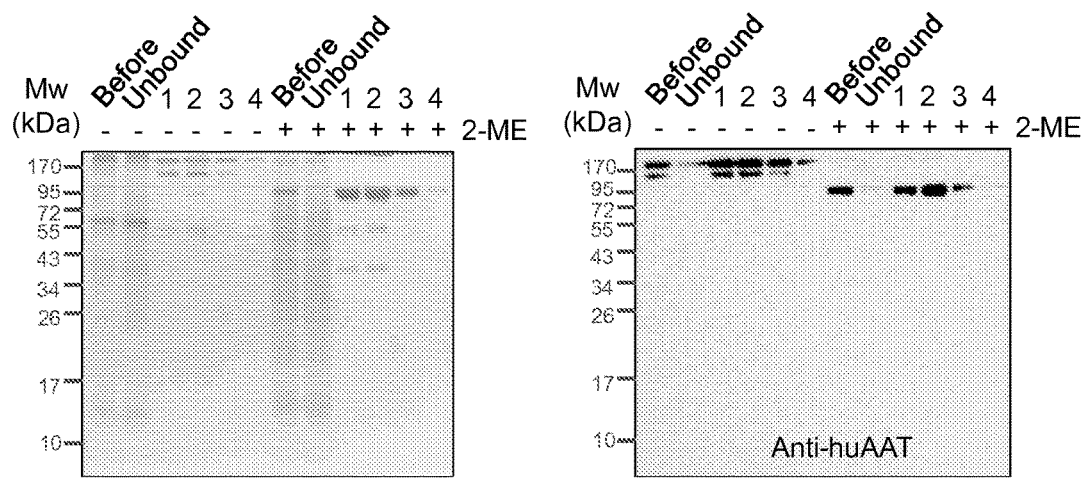
FIG. 2B represents images of a stained gel (left) and a Western blot (right) of fusion molecules of certain embodiments disclosed herein.

Purification of human AAT Fc: A Western blot of the fusion molecules (See for example, FIG. 2B) demonstrated bands (about 170 kDa) that represented an intact dimer of two Fc-AAT molecules. Other lanes on the Western blot represented when all of the disulfide bonds were broken in the fusion molecules to form 2 monomeric molecules of FC-AAT. Both non-reducing gels as well as reducing gels demonstrated high level of purity of the AAT constructs. Therefore, it was demonstrated that Fc-AAT can be purified in a single step from a mammalian cell culture supernatant using protein A chromatography.

Figure 3:
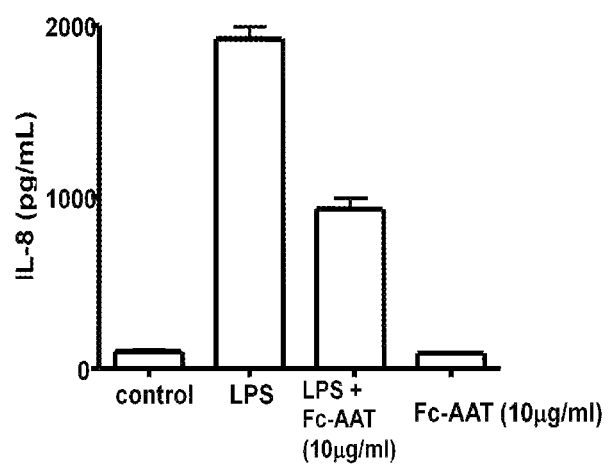
FIG. 3 represents a histogram plot of IL-8 production in a cellular model in the presence or absence of Fc-AAT.

FIG. 3 represents an anti-inflammatory model of the effects of fusion molecules described herein on cytokine expression. In this example, IL-8 expression is measured in the presence or absence of LPS. This model is a well-known model for measuring inflammatory activity in a cell using the stimulator LPS. Human blood neutraphils ($3 \times 10^6$ cells/ml) were incubated for 6 hours alone or in the presence of LPS (10 ng/ml), Fc-AAT (rAAT) at 10 micrograms per milliliter or a combination of LPS and Fc-AAT. IL-8 levels were measured in the culture supernatants (N=3). Neutrophils treated with LPS in the presence of Fc-AAT demonstrated significantly reduced levels of IL-8 compared to LPS alone. Therefore, Fc-AAT demonstrated anti-inflammatory activity.

In certain embodiments disclosed herein, Fc-AAT constructs can have reduced or insignificant serine protease inhibition activity. Other fusion molecules generated herein contain serine protease inhibition activity.

Example 3

Figure 4:
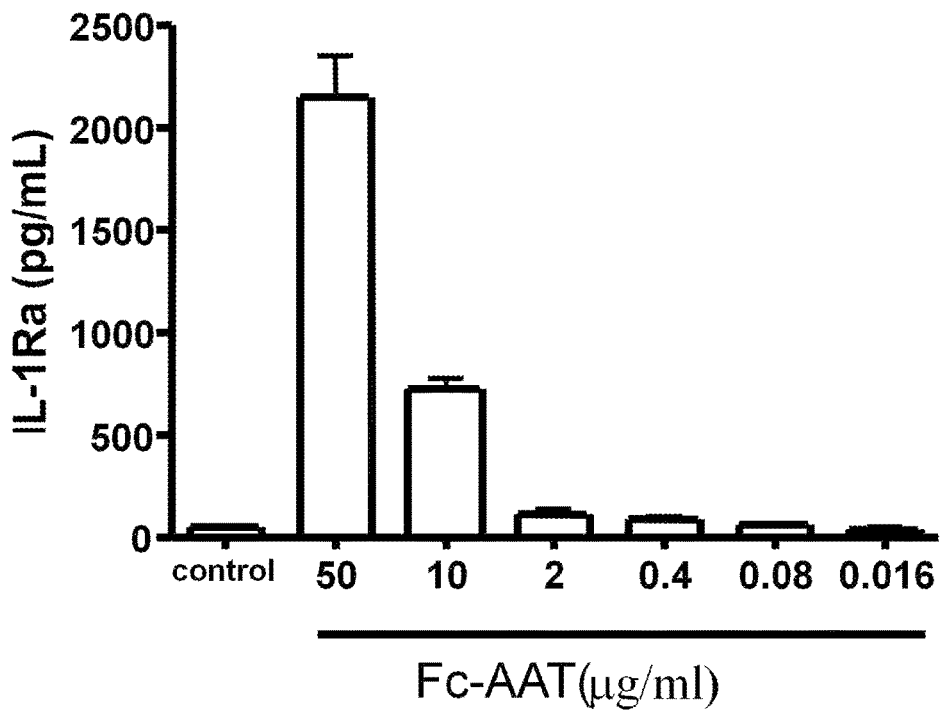
FIG. 4 represents a histogram plot of production of expression of an anti-inflammatory molecule (IL-1 receptor antagonist (IL-1Ra)) in the presence of a fusion molecule of certain embodiments described herein (e.g., Fc-AAT).

FIG. 4 represents a histogram plot using a range of concentrations of a construct described herein on stimulation of an anti-inflammatory molecule, IL-1 receptor antagonist (IL-1Ra). In this exemplary method, neutronphil cells were incubated with decreasing concentrations of a fusion molecule generated herein (e.g., Fc-AAT having a linker region). A control sample was used to demonstrate comparison. These molecules are about 100 times more active than a comparable amount of a commercial formulation (e.g., Aralast™). N=2 in this experiment.

Example 4

Construction of Truncated Variants of Fc-AAT

In certain exemplary embodiments, protease cleavage of AAT can be a simple insertion of a protease site within the sequence of AAT, for example, tobacco mosaic virus protease. Insertion of the protease recognition site generates a truncated carboxyl end of AAT. This site is upstream from a Carboxy-36-terminal peptide of naturally-occurring AAT (see for example, FIG. 5):

```
                                        (SEQ. ID NO. 34)
SIPPEVKFNKPFVFLMIEQNTKSPLFMGKVVNPTQK
```

These truncated AAT molecules are capable of inhibiting LPS-induced IL-1β, IL-6 and TNFα. A bivalent truncated fusion molecule can be superior to the peptide itself in terms of increased plasma half-life. Given the likelihood that natural AAT is found in the lipid rafts of the cell membrane, it would be unlikely that the insertion would be at the N-terminus but rather the C-terminus. Therefore, having the C-terminal 36 amino acids linked to Fc for a bivalent structure will likely be more effective in the lipid rafts. It was demonstrated that the C-36 peptide reduces 18-hour LPS-induced IL-1β at concentrations from 120 µg/mL to 30 µg/mL (data not shown).

Figure 5:
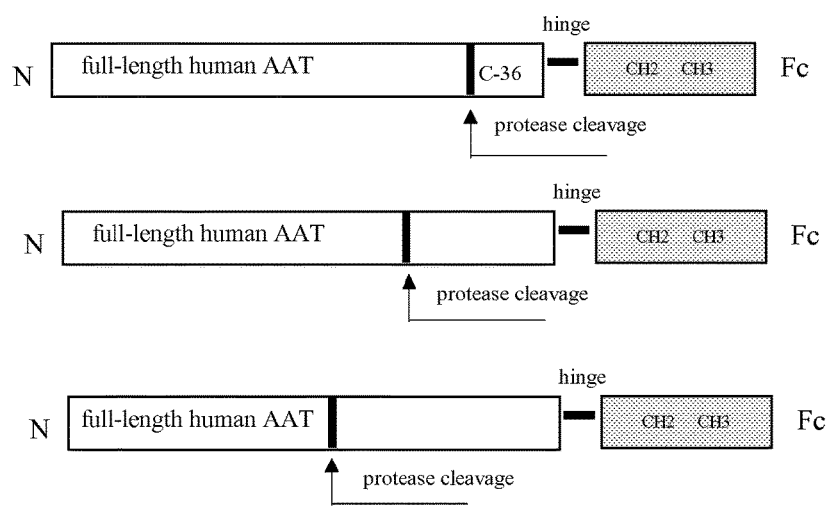
FIG. 5 represents proposed fusion molecules contemplated herein.

The size of the peptide (approximately 4 kDa) will likely have a short half-life therefore, in certain embodiments, it will be formulated with a carrier. Therefore an, Fc invariant region of human IgG1 domain, also called the Fc domain, named for its ability to bind to the complement receptor (FcR) can be used. One advantage of a fusion protein is that it prolongs the half-life in a subject's circulation. Here, there are at least two distinct advantages for the Fc fusion proteins: 1) Easy purification from crude cell supernates using Protein A affinity chromatography; and 2) Fc fusion proteins can be used to treat several diseases in humans and as such, have an established safety record. As illustrated, the effect of other truncated versions of Fc-AAT can readily be assessed. The protease cleavage with, for example, tobacco mosaic virus protease will be performed on the CHO cell supernatants. The mixture will then be applied to a Protein A column and fractions eluted with an acidic buffer, followed by rapid neutralization. Certain truncated Fc-AAT won't have anti-elastase activity. For example, the 36-C peptide does not contain this activity. Therefore, activities of these molecules will be something other than serine protease inhibition activity. These truncated molecules can be larger than the C-36 molecule, such as C-80 or C-60 etc as illustrated in FIG. 5.

Cleavage of the Fc Domain.

Another cleavage site can be that of the Fc itself, in order to remove the Fc fragment from the aAT or AAT-derived peptide, if desired. This site generates a monomeric from of AAT or truncated AAT. However, the enzyme for Fc-IgG1 differs from that of Fc-IgG2 and other IgG molecules contemplated herein.

A Fusion Protein of the N-Terminus.

A construct of N-terminal AAT is a novel concept that is based on data demonstrating that the anti-inflammatory (or anti-immune) properties of AAT are independent of the elastase inhibition property. Thus, using the N-terminal for an inframe construction facilitates the formation of a molecule with a bi-valent C-terminal. For each construct, the expression in CHO is essential as glycosylation is an important component of the molecule. Therefore, CHO cells will be used for the expression of wild-type as well as truncated Fc-AAT.

Purification and Assays of Truncated Fc-AAT.

In the case of a protease insertion site, the protease to cleave the molecule can be introduced first and then use Protein A to isolate only fragments. That would yield a near pure form of product. In certain methods, such as in the case of the Fc cleavage site, the molecule can be purified on Protein A, add the Fc cleavage protease and then remove the Fc fragment on protein A leaving the remaining peptide or protein nearly pure.

Figure 7:
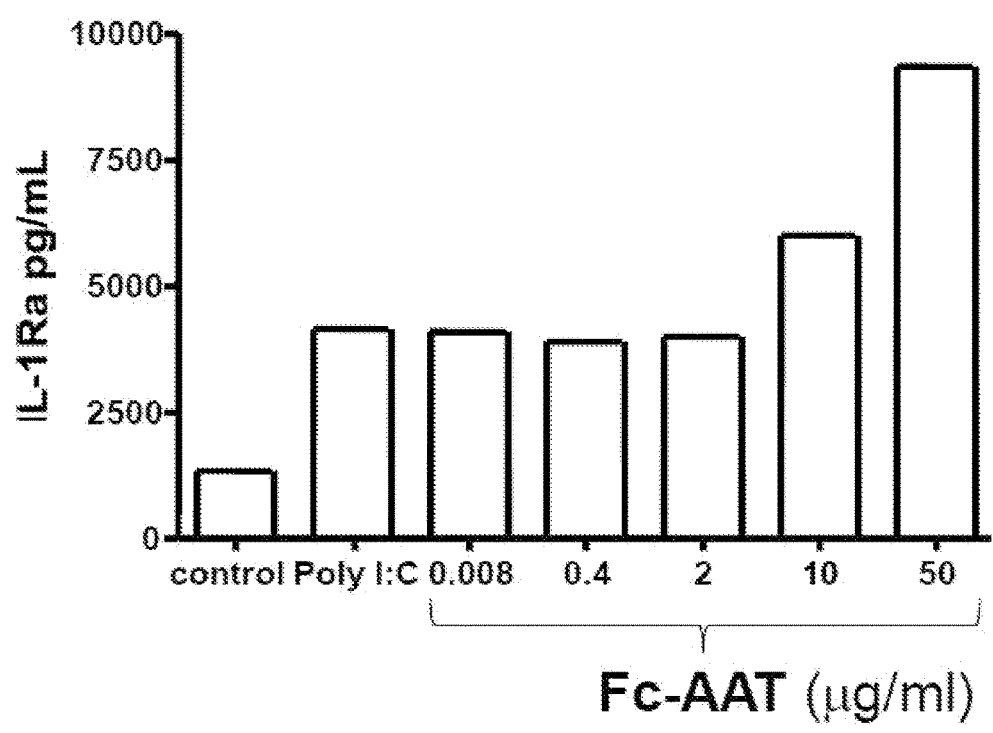
FIG. 7 represents production of IL-1 Receptor antagonist (IL-1Ra) in the presence of increasing amounts of a fusion molecule contemplated herein.

FIG. 7 represents a histogram plot of production of IL-1 Receptor antagonist (IL-Ra) from human blood monocytes in the presence of Fc-AAT (SEQ ID NO:) in the presence of PolyI:C (50 µg/ml) (N=1).

In one exemplary experiment, human blood monocytes were incubated with increasing concentrations of recombinant Fc-AAT or Prolastin C®, (a commercially available form of AAT) in the presence of PolyI:C (50 µg/ml) which mimics a viral infection by inducing large amounts of interferon. In certain cases, those skilled in the art view this model (using PolyI:C) as a more relevant model than using LPS. The concentrations of Fc-AAT and the commercially available AAT formulation ranged from 0.008 to 50 µg/ml. A superior effect was observed on induction of an anti-inflammatory molecule, IL-1 receptor antagonist (IL-1Ra) by Fc-AAT was observed. FIG. 7 represents an exemplary histogram plot demonstrating that at a concentration of 10 µg/ml and 50 µg/ml, the Fc-AAT fusion molecule (with linker) induced about a 1.5 to 2 fold increase in IL-1Ra compared to Prolastin C®.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A nucleic acid construct comprising:
a polynucleotide encoding an alpha-1 antitrypsin (AAT) polypeptide fragment wherein the AAT polypeptide fragment consists of the polypeptide sequence represented by SEQ ID NO:34; a polynucleotide encoding a linker; and a polynucleotide encoding an immunoglobulin Fc polypeptide of IgG2, IgG3, IgG4, or IgD.

2. A nucleic acid construct comprising the construct encoding the fusion polypeptide of SEQ ID NO:48.

3. An isolated vector comprising the nucleic acid construct of claim 1.

4. An isolated cell comprising the vector of claim 3.

5. A nucleic acid construct comprising a polynucleotide encoding an alpha-1 antitrypsin (AAT) polypeptide fragment wherein the alpha-1 antitrypsin (AAT) polypeptide fragment consists of the polypeptide sequence represented by SEQ ID NO:31, a polynucleotide encoding a linker; and a polynucleotide encoding an immunoglobulin Fc polypeptide of IgG2, IgG3, IgG4, or IgD.

6. The nucleic acid construct of claim 5, wherein immunoglobulin Fc polypeptide is IgG4 Fc.

* * * * *

UNITED STATES PATENT AND TRADEMARK OFFICE
CERTIFICATE OF CORRECTION

PATENT NO. : 9,938,353 B2
APPLICATION NO. : 14/125135
DATED : April 10, 2018
INVENTOR(S) : Dinarello et al.

Page 1 of 1

It is certified that error appears in the above-identified patent and that said Letters Patent is hereby corrected as shown below:

In Column 1, Line 12, insert:
-- FEDERALLY FUNDED RESEARCH
This invention was made with government support under grant number AI015614 awarded by National Institutes of Health. The government has certain rights in the invention. --

Signed and Sealed this
Thirty-first Day of July, 2018

Andrei Iancu
*Director of the United States Patent and Trademark Office*